US012383152B2

United States Patent
Kim et al.

(10) Patent No.: US 12,383,152 B2
(45) Date of Patent: Aug. 12, 2025

(54) ELECTRONIC DEVICE INCLUDING MULTIPLE OPTICAL SENSORS AND METHOD FOR CONTROLLING THE SAME

(71) Applicant: Samsung Electronics Co., Ltd., Gyeonggi-do (KR)

(72) Inventors: Taehyeon Kim, Gyeonggi-do (KR); Donguk Kwak, Gyeonggi-do (KR); Daehyeong Lim, Gyeonggi-do (KR); Daeung Jeong, Gyeonggi-do (KR); Jeongmin Park, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 18/606,457

(22) Filed: Mar. 15, 2024

(65) Prior Publication Data
US 2024/0215839 A1 Jul. 4, 2024

Related U.S. Application Data

(63) Continuation of application No. 17/573,046, filed on Jan. 11, 2022, now Pat. No. 12,257,037, which is a (Continued)

(30) Foreign Application Priority Data

Jan. 6, 2021 (KR) ........................ 10-2021-0001595

(51) Int. Cl.
*A61B 5/0225* (2006.01)
*A61B 5/00* (2006.01)
*A61B 5/024* (2006.01)

(52) U.S. Cl.
CPC ...... *A61B 5/02255* (2013.01); *A61B 5/02433* (2013.01); *A61B 5/6802* (2013.01)

(58) Field of Classification Search
None
See application file for complete search history.

(56) References Cited

U.S. PATENT DOCUMENTS

| | | | |
|---|---|---|---|
| 10,114,453 B2 | 10/2018 | Tanaka et al. | |
| 10,206,577 B2 | 2/2019 | Jang et al. | |
| (Continued) | | | |

FOREIGN PATENT DOCUMENTS

| | | |
|---|---|---|
| JP | 2019-525792 | 9/2019 |
| KR | 10-2016-0024627 | 3/2016 |
| (Continued) | | |

OTHER PUBLICATIONS

European Search Report dated Feb. 20, 2024 issued in application No. EP 22736827.1, 9 pages.

(Continued)

*Primary Examiner* — Keith M Raymond
*Assistant Examiner* — Ashish S Jasani
(74) *Attorney, Agent, or Firm* — The Farrell Law Firm, P.C.

(57) ABSTRACT

An electronic device and a method for controlling the electronic device are provided. The electronic device includes a motion sensor and optical sensors. Each of the optical sensors includes a light emitter and a light receiver. The optical sensors are separately driven to determine a respective signal characteristic of each of the optical sensors. A current state of an object to be measured is determined, based on at least one signal received through the motion sensor or the optical sensors. A light emitter of at least one of the optical sensors is driven, based on the respective signal characteristics of the optical sensors according to the current state of the object to be measured. Based on the respective signal characteristics of the optical sensors, a light (Continued)

signal sensed through a light receiver of at least one of the optical sensors is selected and received.

11 Claims, 16 Drawing Sheets

Related U.S. Application Data continuation of application No. PCT/KR2022/000160, filed on Jan. 5, 2022.

(56) References Cited

U.S. PATENT DOCUMENTS

| | | | |
|---|---|---|---|
| 10,264,982 | B2 | 4/2019 | Tanaka et al. |
| 11,771,350 | B1* | 10/2023 | Mannheimer ...... A61B 5/14552 600/323 |
| 2016/0058366 | A1 | 3/2016 | Choi et al. |
| 2016/0077587 | A1 | 3/2016 | Kienzle et al. |
| 2016/0367187 | A1 | 12/2016 | Ahmed et al. |
| 2017/0042485 | A1 | 2/2017 | Chung et al. |
| 2017/0079534 | A1 | 3/2017 | Tchertkov et al. |
| 2017/0331505 | A1 | 11/2017 | Shim et al. |
| 2019/0069781 | A1* | 3/2019 | Kim .................. A61B 5/681 |
| 2019/0167199 | A1 | 6/2019 | Nam et al. |
| 2019/0223787 | A1 | 7/2019 | Kelly et al. |
| 2020/0000345 | A1 | 1/2020 | Connor |
| 2020/0297215 | A1 | 9/2020 | Cho et al. |
| 2020/0297226 | A1 | 9/2020 | LeFrancois et al. |
| 2021/0196135 | A1 | 7/2021 | Takamizawa et al. |

FOREIGN PATENT DOCUMENTS

| | | |
|---|---|---|
| KR | 10-2016-0149489 | 12/2016 |
| KR | 10-2017-0019745 | 2/2017 |
| KR | 10-2017-0055523 | 5/2017 |
| KR | 10-2017-0127744 | 11/2017 |
| KR | 10-2018-0045735 | 5/2018 |
| KR | 10-2018-0056714 | 5/2018 |
| KR | 10-2018-0066503 | 6/2018 |
| KR | 10-1924702 | 2/2019 |
| KR | 10-2019-0027238 | 3/2019 |
| KR | 10-2019-0065089 | 6/2019 |
| KR | 10-2019-0133107 | 12/2019 |
| KR | 10-2020-0134450 | 12/2020 |
| KR | 10-2022-0045278 | 4/2022 |

OTHER PUBLICATIONS

International Search Report dated Apr. 12, 2022 issued in counterpart application No. PCT/KR2022/000160, 20 pages.
U.S. Office Action dated May 3, 2024 issued in counterpart U.S. Appl. No. 17/573,046, 28 pages.
U.S. Final Office Action dated Sep. 25, 2024 issued in U.S. Appl. No. 17/573,046, 18 pages.

* cited by examiner

ELECTRONIC DEVICE INCLUDING MULTIPLE OPTICAL SENSORS AND METHOD FOR CONTROLLING THE SAME

CROSS-REFERENCE TO RELATED APPLICATIONS

This application is a Continuation application of U.S. patent application Ser. No. 17/573,046, filed in the U.S. Patent and Trademark Office on Jan. 11, 2022, which is a bypass continuation application, claiming priority under § 365(c) to International Application No. PCT/KR2022/000160, filed on Jan. 5, 2022, which is based on and claims priority to Korean Patent Application Serial No. 10-2021-0001595, filed on Jan. 6, 2021 in the Korean Intellectual Property Office, the disclosures of each of which are incorporated herein by reference in its entirety.

BACKGROUND

1. Field

The disclosure is generally related to an electronic device including multiple optical sensors, and more particularly, to an electronic device including multiple optical sensors which may be worn on a user's body so as to acquire the user's biometric information.

2. Description of Related Art

Electronic devices have evolved to have smaller sizes and to be able to perform various functions in various manners according to user needs. Such electronic devices may include, for example, various types of wearable devices that can be directly attached to a part of the user's body.

Such wearable devices are used to acquire various pieces of information from the user's body, and various services are provided based thereon.

A wearable electronic device, such as, for example, a ring-type wearable electronic device worn on a finger, may be equipped with a photoplethysmography (PPG) sensor so as to acquire information from the user's body, to calculate information such as heart rate, stress, blood oxygen saturation (SpO2), and blood pressure based thereon, and to provide the same to the user.

A wearable electronic device, such as, for example, a ring-type wearable electronic device, may easily spin when worn on the user such that, even if multiple optical sensors are employed, the position of each optical sensor may frequently change, thereby making accurate measurement difficult.

SUMMARY

Embodiments described herein may provide a method in which, in connection with an electronic device including multiple optical sensors, each optical sensor is controlled based on signal characteristics of each of the multiple optical sensors, and the electronic device.

According to an aspect, an electronic device is provided that includes a housing, a motion sensor, and optical sensors disposed on one surface of the housing so as to be brought into contact with an object to be measured when the electronic device is worn. Each of the optical sensors comprises a respective light emitter and a respective light receiver. The electronic device also includes a sensor controller configured to control the optical sensors, and a processor operatively connected to the motion sensor and the sensor controller. The processor is configured to separately drive the optical sensors through the sensor controller to determine a respective signal characteristic of each of the optical sensors, and determine a current state of the object to be measured, based on at least one signal received through the motion sensor or the optical sensors. The processor is also configured to drive a light emitter of at least one of the optical sensors through the sensor controller, based on the respective signal characteristics of the optical sensors according to the current state of the object to be measured, and select and receive, based on the respective signal characteristics of the optical sensors, a light signal sensed through a light receiver of at least one of the optical sensors.

According to an aspect, a method is provided for controlling an electronic device including a motion sensor and optical sensors. Each of the optical sensors includes a light emitter and a light receiver. The optical sensors are separately driven to determine a respective signal characteristic of each of the optical sensors. A current state of an object to be measured is determined, based on at least one signal received through the motion sensor or the optical sensors. A light emitter of at least one of the optical sensors is driven, based on the respective signal characteristics of the optical sensors according to the current state of the object to be measured. Based on the respective signal characteristics of the optical sensors, a light signal sensed through a light receiver of at least one of the optical sensors is selected and received.

Signal characteristics of multiple optical sensors which may change according to a wearing state of an electronic device are identified, and the multiple optical sensors may be individually controlled based thereon, thereby acquiring more accurate measurement values.

Multiple optical sensors may be individually controlled based on signal characteristics of the multiple optical sensors according to a usage state of an electronic device, thereby acquiring more accurate measurement values.

Multiple optical sensors may be controlled in view of signal characteristics of the multiple optical sensors based on an event type when a designated event occurs according to a usage state of an electronic device, thereby acquiring more accurate measurement values.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
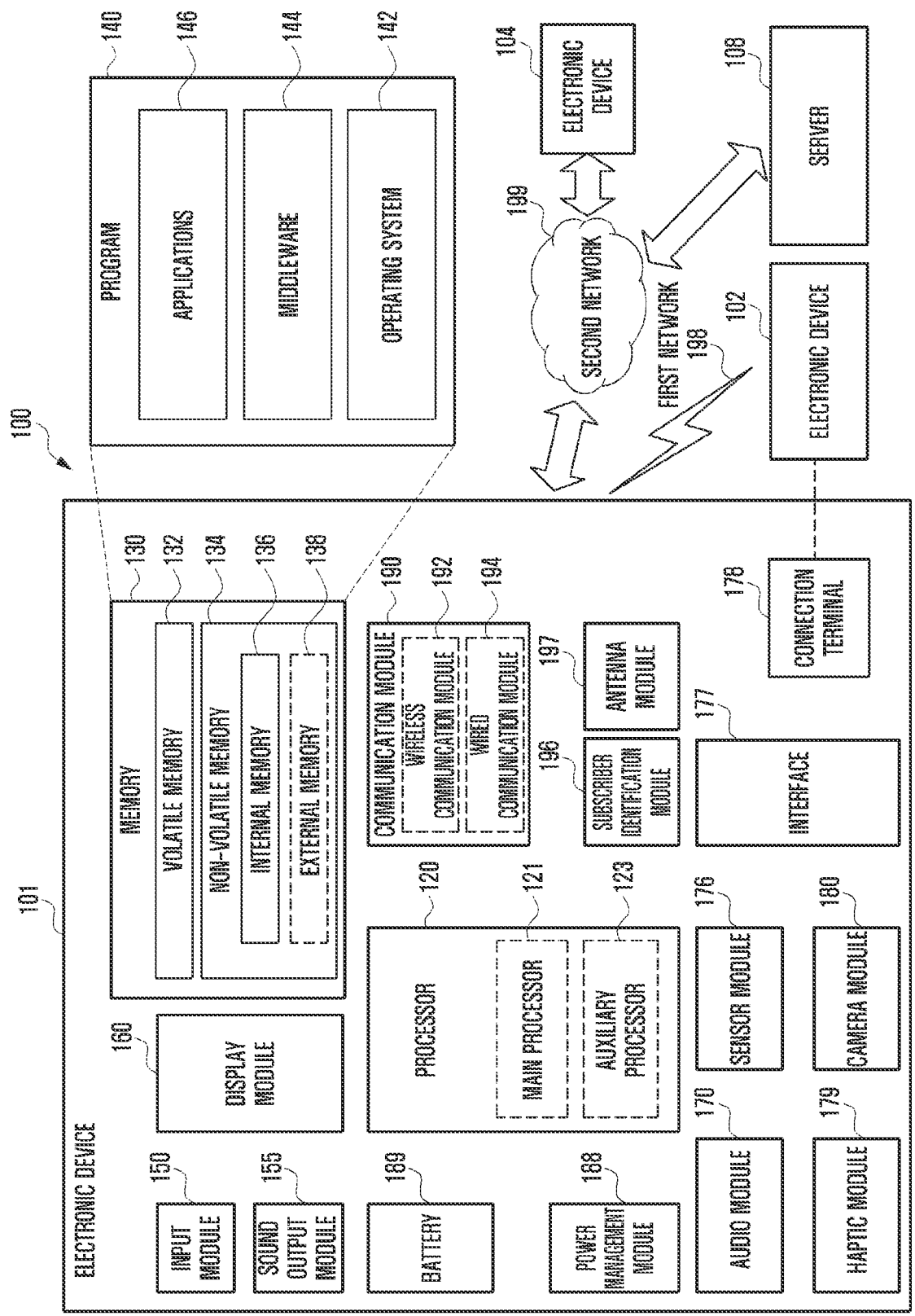
FIG. 1 is a block diagram illustrating an electronic device in a network environment; according to an embodiment.

Embodiments are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the disclosure. The embodiments and the terms used herein are not intended to limit the technology disclosed herein to specific forms, and should be understood to include various modifications, equivalents, and/or alternatives to the corresponding embodiments. A singular expression may include a plural expression unless they are definitely different in context.

FIG. 1 is a block diagram illustrating an electronic device in a network environment, according to an embodiment. Referring to FIG. 1, an electronic device 101 in a network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module).

A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra-low latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

A method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™) or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
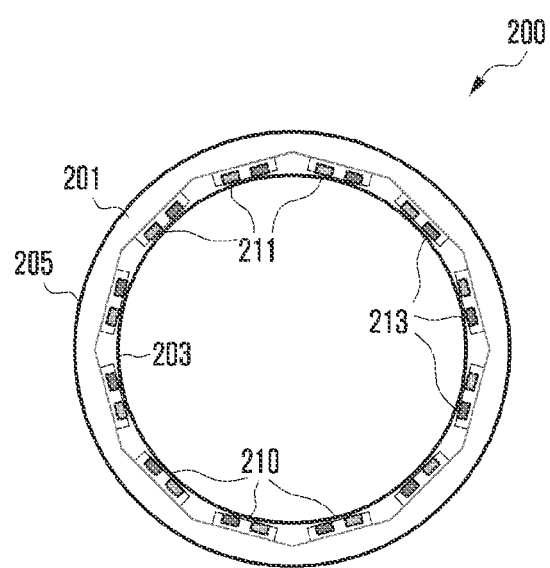
FIGS. 2A and 2B are diagrams illustrating exterior shapes of an electronic device having multiple optical sensors, according to an embodiment.
Figure 2B:
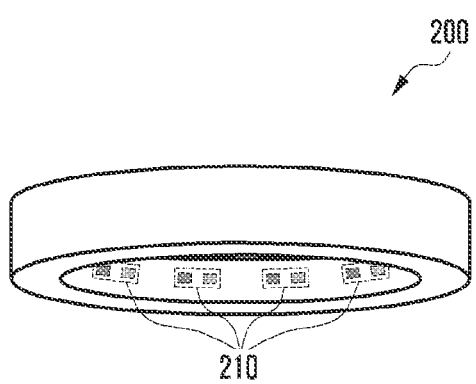

FIGS. 2A and 2B are diagrams illustrating exterior shapes of an electronic device, according to an embodiment.

As illustrated in FIGS. 2A and 2B, an electronic device 200 may be a wearable device that can be worn on a finger. However, the electronic device 200 is not limited thereto. Various types of electronic devices, each of which having an optical sensor module (e.g., a PPG sensor) mounted thereto and acquiring biometric information of a user, may correspond to the electronic device 200 described herein. For example, the electronic device 200 may also be implemented as various wearable devices such as body-attachable devices (e.g., health patches or digital tattoos), clothing-type devices (e.g., smart clothing or gloves), or band-type devices (e.g., wrist/arm/finger bands or smart rings).

As illustrated in FIGS. 2A and 2B, the electronic device 200 includes a housing 201. The housing 201 may be implemented in a ring shape so as to at least partially surround the outer surface of an object to be measured (e.g., a finger of a user) when being worn, thereby preventing the housing 201 from being separated by the movement of the object to be measured.

The housing 201 includes a first surface 203, which is an inner surface brought into contact with the outer surface of a part of the user's body when the user wears the electronic device. The housing also includes a second surface 205, which is an outer surface viewable from the outside when the user wears the electronic device.

The electronic device 200 includes multiple optical sensors 210. The multiple optical sensors 210 are mounted on the first surface 203 of the housing 201 so as to be brought into contact with the outer surface of a part of the user's body, and so as to emit at least light in the inward direction of the housing 201. For example, when the user wears the electronic device 200, the multiple optical sensors 210 may emit light to the outer surface of a part of the user's body placed in the inward direction of the housing 201, and may sense light reflected therefrom.

The multiple optical sensors 210 may include at least one PPG sensor. In the PPG sensor, a light receiver 213 (e.g., a photodiode) may at least partially sense reflected light when light output by a light emitter 211 (e.g., a light emitting diode (LED)) is reflected by an external object (e.g., a finger of the user). The electronic device 200 may acquire, biometric information such as heart rate, stress, and blood oxygen saturation of ($SpO_2$) of the user, based on the reflected light sensed by the at least one light receiver 213.

The multiple optical sensors 210 may be viewable from the outside through at least a part of the housing 201.

The multiple optical sensors 210 may be arranged in a ring shape of a one-column array at designated intervals (e.g., identical intervals or different intervals) along the first surface 203 of the housing 201, for example, along the inner circumference thereof. The number and/or arrangement of the multiple optical sensors 210 is not limited to those illustrated, and various numbers of optical sensors 210 may be arranged in consideration of the size or shape (e.g., the circumferential length and width) of the housing 201 of the electronic device 200. Furthermore, the multiple optical sensors 210 may be arranged in various forms in consideration of the size and/or sensing efficiency of the optical sensors 210.

Each of the multiple optical sensors 210 may include at least one light emitter 211 and at least one light receiver 213. As illustrated in FIGS. 2A and 2B, each optical sensor 210 includes one light emitter 211 and one light receiver 213, but the number and/or arrangement of light emitters 211 and light receivers 213, included in each optical sensor 210, may not be limited thereto. For example, each optical sensor 210 may include multiple light emitters 211 and/or multiple light receivers 213.

The light emitter 211 included in each of the multiple optical sensors 210 may output light of a visible light band (e.g., green, red, blue) and/or an infrared band (e.g., infrared). For example, the light emitter 211 may output blue light having a wavelength of about 400 nm to about 550 nm, green light having a wavelength of about 450 nm to about 650 nm, red light having a wavelength of about 550 nm to about 700 nm, and/or infra-red (IR) light having a wavelength of about 880 nm to about 940 nm. When green light is used, the green light may be not sensitive to motion, but may have low skin transmissivity. When red light or IR is used, the red light or IR light may have high skin transmissivity, but may have a low signal intensity and may be sensitive to motion.

The light emitter 211 included in each of the multiple optical sensors 210 may be implemented so as to be able to output light of various wavelength bands and/or various intensities. For example, the light emitter 211 included in each of the multiple optical sensors 210 may include multiple light-emitting elements (e.g., LEDs) capable of outputting at least one of green light, red light, and/or IR light. For example, the light emitter 211 may include at least one among an LED, an organic LED (OLED), a laser diode (LD), a solid laser, and an infrared (IR) diode.

The light receiver 213 included in each of the multiple optical sensors 210 may include various elements capable of sensing a light signal, converting the light signal to an electrical signal, and outputting the electrical signal. For example, the light receiver 213 may include at least one among a photo diode (PD), an avalanche PD (APD), a phototransistor, and an image sensor.

An optical sensor module may further include an analog front end (AFE), such as, for example, an amplifier, a band pass filter (BPF), and/or an analog-to-digital converter (ADC), for processing the electrical signal output by the light receiver 213.

The electronic device 200 may filter the electrical signal output by the light receiver 213 through analog control, such as, for example, offset correction and gain adjustment, using the AFE, and then may acquire biometric row data in the form of a digital signal. The electronic device 200 may calculate, based on the biometric raw data, biometric information such as the heart rate, stress, and blood oxygen saturation ($SpO_2$) of the user.

The light receiver 213 included in each of the multiple optical sensors 210 may sense reflected light of at least a part of the light output by the light emitter 211 included in the same optical sensor 210 among the multiple optical sensors 210, may sense reflected light of at least a part of light output by a light emitter 211 included in a different optical sensor 210, and/or may sense reflected light of at least a part of light output by all light emitters 211 included in the multiple optical sensors 210. The principle of acquiring biometric information of a user using the optical sensors 210 is described in greater detail below with reference to FIG. 3.

A display may be disposed on the second surface 205 (e.g., a surface viewable from the outside when the user wears the electronic device) of the housing 201. For example, the display may display various application screens, such as, for example, time information, a message, or a call.

The electronic device 200 may further include a motion sensor. The motion sensor may include various types of sensors capable of sensing motion of the electronic device 200, such as, for example, a gyro sensor, an acceleration sensor, or a geomagnetic sensor. The motion sensor may acquire at least one sensing signal changing depending on the motion of a user wearing the electronic device 200. The electronic device 200 may determine, based on the sensing signal of the motion sensor, the degree of motion of the electronic device 200 and/or the user wearing the electronic device 200.

Figure 3:
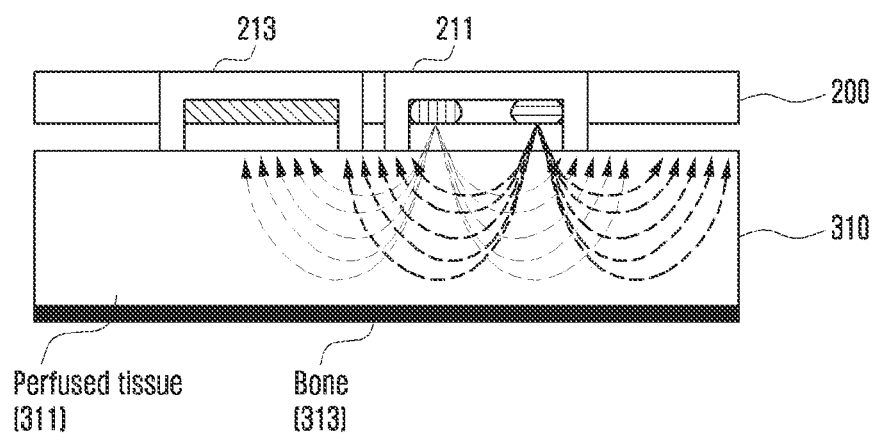
FIG. 3 is a diagram illustrating a principle of an optical sensor, according to an embodiment.

FIG. 3 is a diagram illustrating a principle of an optical sensor, according to an embodiment.

FIG. 3 illustrates a principle by which reflected light of at least a part of light, which has been output from light-emitting elements of the light emitter 211, has hit an external object 310 (e.g., a user's finger), and then has been reflected, is sensed through the light receiver 213 while a user wears the electronic device 200. FIG. 3 illustrates an optical sensor which includes the light emitter 211 having two light-emitting elements, and the light receiver 213. However, as described above, the electronic device 200 may include multiple optical sensors 210, and each optical sensor may include multiple light emitters 211 and light receivers 213.

The light emitter 211 may output light of a designated wavelength band (e.g., green, red, blue, IR), based on a control signal of a processor. Light output by the light emitter 211 may be reflected by a perfused tissue 311 and/or a bone 313, and the properties of a reflected light signal received by the light receiver 213 may vary depending on the user's body condition. For example, when blood flowing through a blood vessel of the user's wrist increases, the blood vessel dilates, and thus, the amount of reflected light, which is reflected and sensed by the light receiver 213, may decrease. Therefore, the electronic device 200 may measure biometric information such as the heart rate, stress, and blood oxygen saturation ($SpO_2$) of the user based on the properties of the reflected light sensed by the light receiver 213.

Figure 4:
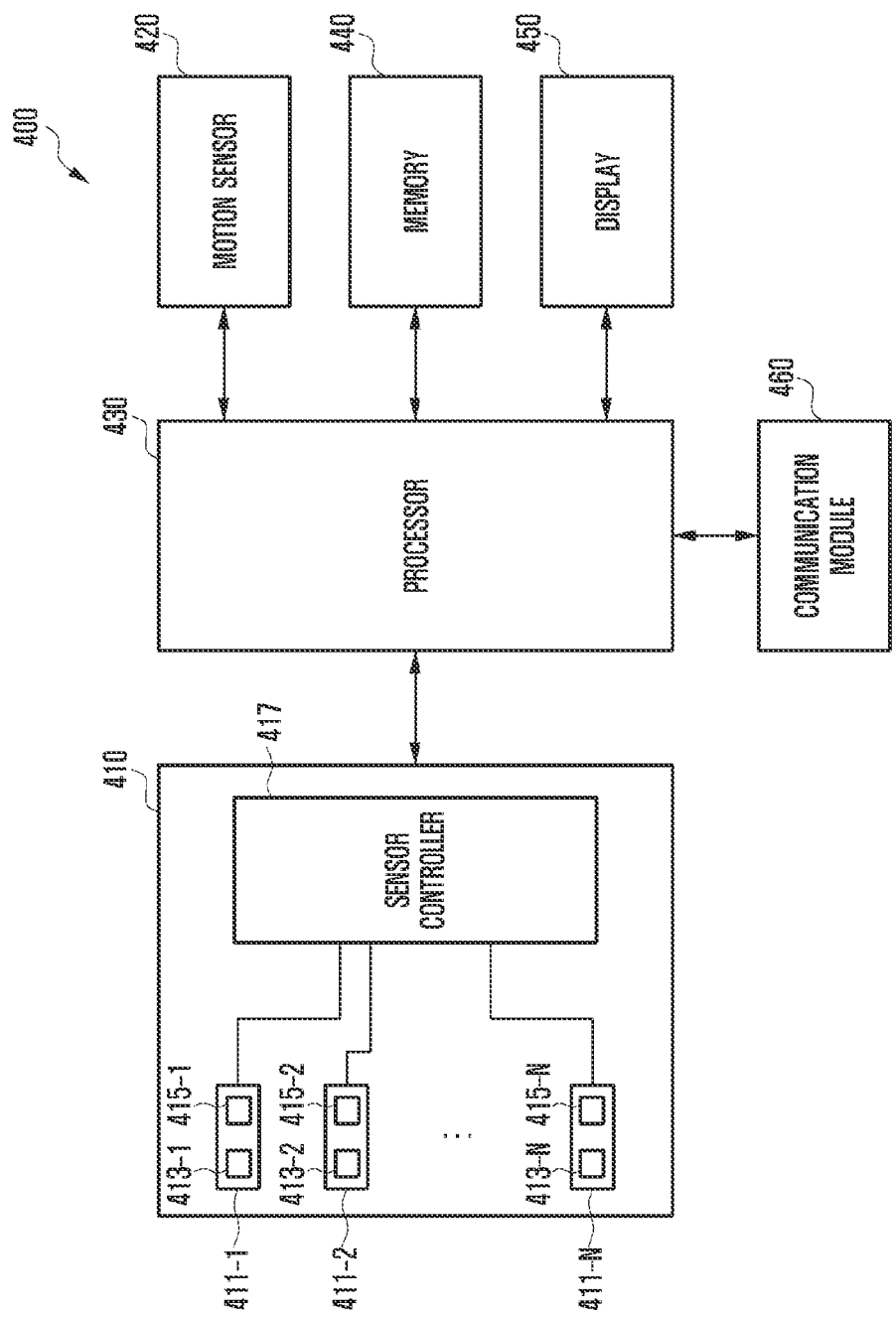
FIG. 4 is a block diagram illustrating an electronic device having multiple optical sensors, according to an embodiment.

FIG. 4 is a block diagram illustrating an electronic device, according to an embodiment.

As illustrated in FIG. 4, an electronic device 400 includes an optical sensor module 410, a motion sensor 420, a processor 430, a memory 440, a display 450, and a communication module 460. The elements illustrated in FIG. 4 are merely an example, and some elements may be omitted or replaced, or may be integrated as a single module.

The electronic device 400 may include the wearable electronic device 200 described above through FIGS. 2A and 2B, but is not limited thereto. Thus, various types of electronic devices, which include the optical sensor module 410 and can acquire biometric information of a user, may correspond to the electronic device 400. For example, the electronic device 400 may include wearable devices such as a body-attachable device (e.g., a health patch, or a digital tattoo), a clothing device (e.g., smart clothing or gloves), and a band-type device (e.g., a wrist/arm/finger band, or a smart ring).

The optical sensor module 410 includes multiple optical sensors 411-1, 411-2, . . . , 411-N. The multiple optical sensors 411-1, 411-2, . . . , 411-N included in the optical sensor module 410 include respective light emitters 413-1, 413-2, . . . , 413-N and respective light receivers 415-1, 415-2, . . . , 415-N.

As described with reference to FIGS. 2A and 2B, the multiple optical sensors 411-1, 411-2, . . . , 411-N of the optical sensor module 410 may be arranged in a line at a predetermined interval along the circumference of the inner surface of a housing of the electronic device 400, and may be brought into contact with (or may approach) the surface of a part of the user's body when the user wears the electronic device 400.

Each of the light emitters 413-1, 413-2, . . . , 413-N included in the respective optical sensors 411-1, 411-2, . . . , 411-N may include multiple light-emitting elements in order to output light having a designated wavelength band and/or different light intensities and including green light, red light, blue light and/or IR light. Each optical sensor is shown to include one light emitter 413-1, 413-2, . . . , 413-N, but there may be more than one light emitter included in each optical sensor. Each of the light receivers 415-1, 415-2, . . . , 415-N included in the multiple optical sensors 411-1, 411-2, . . . , 411-N may include at least one light-receiving element (e.g., a PD, an APD, a phototransistor, or an image sensor) capable of sensing a light signal, converting the light signal to an electrical signal, and outputting the electrical signal. Each optical sensor is shown to include one light receiver 415-1, 415-2, . . . , 415-N, but there may be more than one light receiver included in each optical sensor.

The optical sensor module 410 may be electrically connected to the processor 430, and each of the multiple optical sensors 411-1, 411-2, . . . , 411-N may independently operate based on a control signal of the processor 430.

The multiple optical sensors 411-1, 411-2, ..., 411-N may be controlled to operate at different timings, based on a control signal of the processor 430, or the multiple optical sensors may be controlled to operate at a substantially identical timing. For example, the respective light emitters 413-1, 413-2, ..., 413-N of the multiple optical sensors 411-1, 411-2, ..., 411-N may be controlled to sequentially emit light at different timings, respectively, or all of the light emitters 413-1, 413-2, ... 413-N may be controlled to emit light at a substantially identical timing.

Operations of the respective light emitters 413-1, 413-2, ..., 413-N and the respective light receivers 415-1, 415-2, ..., 415-N of the multiple optical sensors 411-1, 411-2, ..., 411-N may be independently controlled based on the control signal of a processor 430.

Each of the light receivers 415-1, 415-2, ..., 415-N of the multiple optical sensors 411-1, 411-2, ..., 411-N may receive, when light is emitted from a light emitter of an identical optical sensor among the respective light emitters 413-1, 413-2, ..., 413-N of the multiple optical sensors 411-1, 411-2, ..., 411-N, a light signal received by reflection of the emitted light. For example, a light receiver 415-$n$ of an optical sensor (e.g., 411-$n$, 1≤n≤N) may receive a light signal when light emitted by a light emitter 413-$n$ of the optical sensor 411-$n$ is reflected and received.

Each of the light receivers 415-1, 415-2, ..., 415-N of the multiple optical sensors 411-1, 411-2, ..., 411-N may receive, even when light is emitted from light emitters of other optical sensors among the respective light emitters 413-1, 413-2, ..., 413-N of the multiple optical sensors 411-1, 411-2, ..., 411-N, light signals received by reflection of the emitted light. For example, a light receiver (415-$n$) of an optical sensor (e.g., 411-$n$, 1≤n≤N) may receive a light signal received by reflection of light emitted by a light emitter (413-$m$) of another optical sensor (e.g., 411-$m$, 1≤m≤N, m≠n) different from the optical sensor (411-$n$).

When light is emitted from all the light emitters 413-1, 413-2, ..., 413-N of the multiple optical sensors 411-1, 411-2, ..., 411-N, the respective light receivers 415-1, 415-2, ..., 415-N of the multiple optical sensors 411-1, 411-2, ..., 411-N may receive light signals received by reflection of the emitted light. For example, when the respective light emitters 413-1, 413-2, ..., 413-N of the multiple optical sensors 411-1, 411-2, ..., 411-N emit light while being controlled to substantially simultaneously emit light, reflected light signals may be received by the respective light receivers 415-1, 415-2, ..., 415-N.

The optical sensor module 410 further includes a sensor controller 417 electrically connected to the multiple optical sensors 411-1, 411-2, ..., 411-N and capable of independently controlling an operation of each of the optical sensors.

The sensor controller 417 may operate as an analog front end for processing a light signal received from the multiple optical sensors 411-1, 411-2, ..., 411-N and transmitting the light signal to the processor 430. For example, the sensor controller 417 may perform a signal pre-processing process through filtering such as gain control and/or offset correction with respect to an electrical signal converted from the light signal received from the multiple optical sensors 411-1, 411-2, ... 411-N, and may convert the electrical signal to a digital signal.

The sensor controller 417 may be operatively connected to the processor 430 and the multiple optical sensors 411-1, 411-2, ..., 411-N, and may function as an interface for controlling signal transmission/reception between the processor 430 and the multiple optical sensors 411-1, 411-2, ..., 411-N. For example, the sensor controller 417 may receive a control signal of the processor 430 to drive a light emitter (413-$n$) of at least one optical sensor (e.g., 411-$n$, 1≤n≤N) among the multiple optical sensors 411-1, 411-2, ..., 411-N, such that the light emitter emits light having a designated intensity in a designated wavelength band. For example, the sensor controller 417 may receive a control signal of the processor 430 to process a light signal sensed by a light receiver (415-$m$) of at least one optical sensor (e.g., 411-$m$, 1≤m≤N) among the multiple optical sensors 411-1, 411-2, ..., 411-N, and may provide the processed light signal to the processor 430.

The motion sensor 420 may include various types of sensors capable of sensing the motion of the electronic device 400, such as gyro sensor and an acceleration sensor. The motion sensor 420 may be electrically connected to the processor 430, and may provide, to the processor 430, a motion signal generated based on sensing of the motion of the electronic device 400.

The memory 440 may include a volatile memory and/or a nonvolatile memory 440, may be electrically connected to the processor 430, and may store various instructions executed by the processor 430. The instructions may include a control command, such as arithmetic and logic calculation, data movement, or an input/output, which can be recognized by a control circuit, and may be defined on a framework stored in the memory 440. Furthermore, the memory 440 may store at least a part of the program 140 in FIG. 1.

The processor 430 may perform calculation or data processing regarding communication and/or control of each of the elements of the electronic device 400, and may include at least a part of the configuration and/or function of the processor 120 in FIG. 1. For example, the processor 430 may be electrically connected to the optical sensor module 410, the motion sensor 420, the memory 440, the display 450, and the communication module 460 to control these elements and/or process calculation and/or data related to operations of these elements.

The processor 430 may load the instructions stored in the memory 440, and may control the elements of the electronic device 400 to perform operations of implementing various embodiments based on the loaded instructions and/or may process calculation and/or data related to operations of these elements.

The processor 430 may use the optical sensor module 410 to acquire a bio-signal from a part of a user's body (e.g., a user's finger), and may calculate, based on the bio-signal, biometric information such as the heart rate, stress, and blood oxygen saturation ($SpO_2$) of the user.

In order to acquire desired biometric information, the processor 430 may determine, based on signals sensed by the optical sensor module 410 and/or the motion sensor 420, the current state (e.g., a normal state, a sleep state, an exercise state, or an event occurrence state) of the user wearing the electronic device 400.

The processor 430 may control, based on the determined current state of the user, the sensor controller 417 of the optical sensor module 410 such that, based on signal characteristics of the multiple optical sensors 411-1, 411-2, ..., 411-N, the light emitter (413-$n$) of the at least one optical sensor (e.g., 411-$n$, 1≤n≤N) emits light and such that a reflected and received light signal is received through the light receiver (415-$m$) of the at least one optical sensor (e.g., 411-$m$, 1≤m≤N).

The display 450 may include at least a part of the configuration and/or function of the display module in FIG.

1. For example, the display 450 may include a liquid crystal display (LCD), an LED display, or an OLED display.

The display 450 may provide various types of visual information related to biometric information acquired by the processor 430. For example, the display 450 may display various types of visual information generated based on biometric information or a necessary visual notification in relation to biometric information acquisition.

The communication module 460 may include at least a part of the configuration and/or function of the communication module 190 in FIG. 1. For example, the communication module 460 may provide, under control of the processor 430, communication with various external electronic devices (e.g., the electronic devices 102 and 104 or the server 108 in FIG. 1). For example, the electronic device 400 may perform short-range wireless communication by using the communication module 460. The electronic device 400 may communicate with at least one external electronic device 102, 104, or 108, based on near field communication (NFC), Bluetooth, Bluetooth low energy (BLE), Wi-Fi Direct, and/or ultra-wideband (UWB) communication. In another example, the electronic device 400 may perform long-range wireless communication by using the communication module 460. The electronic device 400 may be connected to an external network (e.g., a cellular network) by using the communication module 460.

Figure 5:
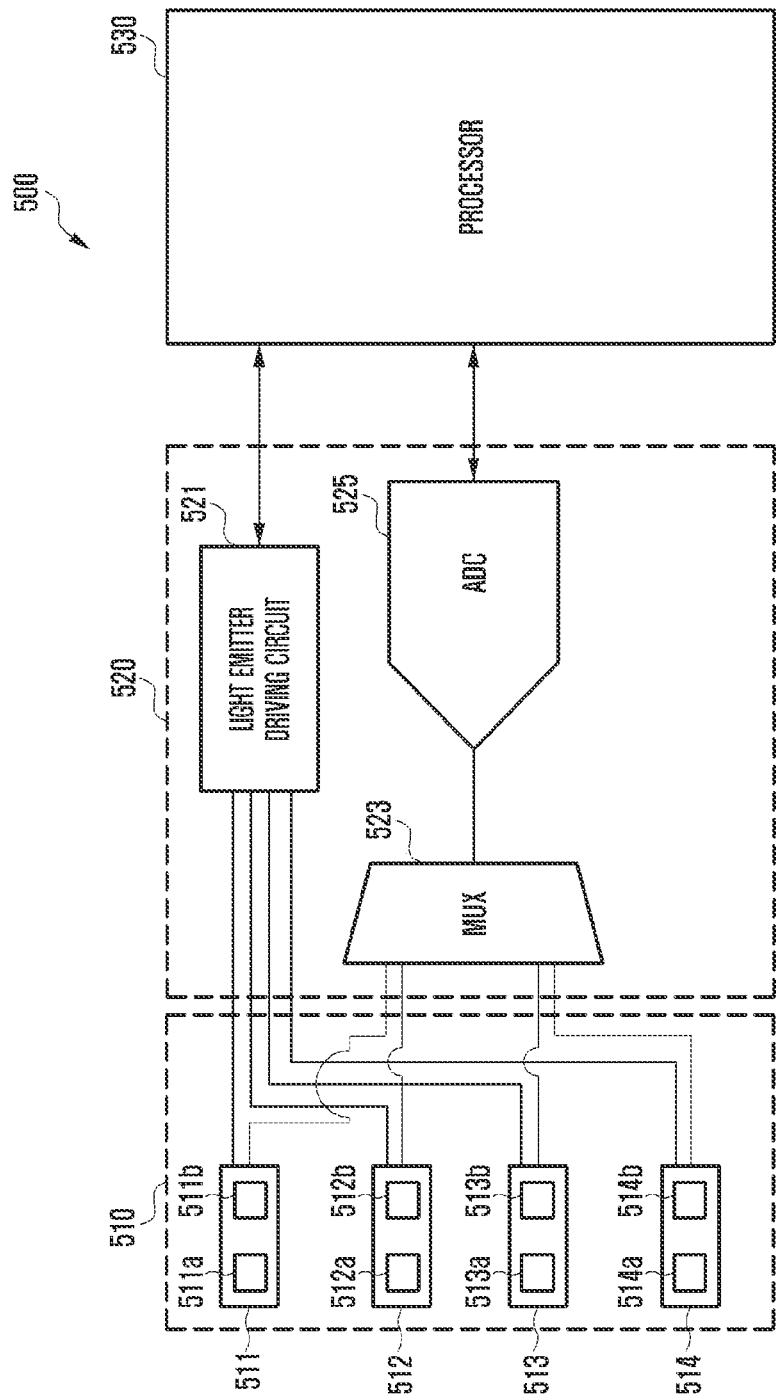
FIG. 5 is a block diagram illustrating an optical sensor module of an electronic device having multiple optical sensors, according to an embodiment.

FIG. 5 is a block diagram illustrating an optical sensor module of an electronic device, according to an embodiment.

FIG. 5 illustrates the circuit structure of an optical sensor unit 510 and a sensor controller 520 for controlling the optical sensor unit of an optical sensor module of an electronic device 500.

For example, the optical sensor unit 510 includes multiple optical sensors (e.g., a first optical sensor 511, a second optical sensor 512, a third optical sensor 513, and a fourth optical sensor 514). Four optical sensors are illustrated as an example, however, the number of multiple optical sensors is not limited, and various numbers of optical sensors may be adopted.

As illustrated in FIG. 5, each of the optical sensors 511, 512, 513, and 514 of the multiple optical sensors may include one light emitter (e.g., a first light emitter 511a, a second light emitter 512a, a third light emitter 513a, and a fourth light emitter 514a) and one light receiver (e.g., a first light receiver 511b, a second light receiver 512b, a third light receiver 513b, and a fourth light receiver 514b), respectively. Each of the optical sensors has been illustrated as including one light emitter and one light receiver, but embodiments are not limited thereto. Each of the optical sensors may be implemented so as to have at least two light emitters and/or at least two light receivers.

The sensor controller 520 is electrically provided between a processor 530 and the optical sensor unit 510, and may control the multiple optical sensors 511, 512, 513, and 514 based on a control signal of the processor 530 to drive the respective light emitters 511a, 512a 513a, and 514a. The sensor controller 520 may provide, to the processor 530, signals received from the respective light receivers 511b, 512b, 513b, and 514b. For example, the sensor controller 520 may include the sensor controller 417 described with reference to FIG. 4. Under control of the processor 530, the sensor controller 520 may emit light through at least one light emitter 511a, 512a, 513a, or 514a of the multiple optical sensors 511, 512, 513, and 514, and may perform a signal pre-processing process through filtering, such as, for example, gain control and/or offset correction, with respect to a light signal received through at least one light receiver 511b, 512b, 513b, or 514b, to convert the light signal to a digital signal.

The sensor controller 520 includes a light emitter driving circuit 521, a multiplexer (MUX) 523, and an analog-to-digital converter (ADC) 525.

The light emitter driving circuit 521 may drive, based on a control signal of the processor 530, at least one light emitter, for example, the first light emitter 511a, the second light emitter 512a, the third light emitter 513a, and/or the fourth light emitter 514a, of the multiple optical sensors, for example, the first optical sensor 511, the second optical sensor 512, the third optical sensor 513, and/or the fourth optical sensor 514.

The first light emitter 511a, the second light emitter 512a, the third light emitter 513a, and/or the fourth light emitter 514a may have various output intensities and output wavelengths. For example, the first light emitter 511a, the second light emitter 512a, the third light emitter 513a, and/or the fourth light emitter 514a may have multiple light-emitting elements having different attributes in output intensity and/or output wavelength. The control signal, which the sensor controller 520 (or, the light emitter driving circuit 521) receives from the processor 530, may include information about a light emitter to be driven and information about the output intensity and/or output wavelength of light that is to be output by the light emitter to be driven.

The first light receiver 511b, the second light receiver 512b, the third light receiver 513b, and/or the fourth light receiver 514b of the multiple optical sensors may sense the amount of light and may output an analog electrical signal (hereinafter, referred to as "light signal") corresponding to the sensed amount of light. For example, each of the first light receiver 511b, the second light receiver 512b, the third light receiver 513b, and/or the fourth light receiver 514b may include at least one light-receiving element (e.g., a PD, an APD, a phototransistor, and/or an image sensor) capable of sensing the amount of light and outputting an analog electrical signal corresponding to the sensed amount of light.

A light signal that is output from each of the first light receiver 511b, the second light receiver 512b, the third light receiver 513b, and/or the fourth light receiver 514b of the multiple optical sensors may be input into the MUX 523, and the MUX 523 may transfer, under control the processor 530, the light signal to the processor 530 through the ADC 525. For example, the MUX 523 may output signals transferred from the light receivers 511b, 512b, 513b, and 514b to the ADC 525 through separate respective channels. The MUX 523 may output some signals selected from among signals transmitted from the respective light receivers 511b, 512b, 513b, and 514b to the ADC 525 through corresponding channels. The MUX 523 may output all of the signals transmitted from the respective light receivers 511b, 512b, 513b, and 514b to the ADC 525 through corresponding channels. All of the signals transmitted from the respective light receivers 511b, 512b, 513b, and 514b may be outputted to the ADC 525 through one channel.

Figure 6:
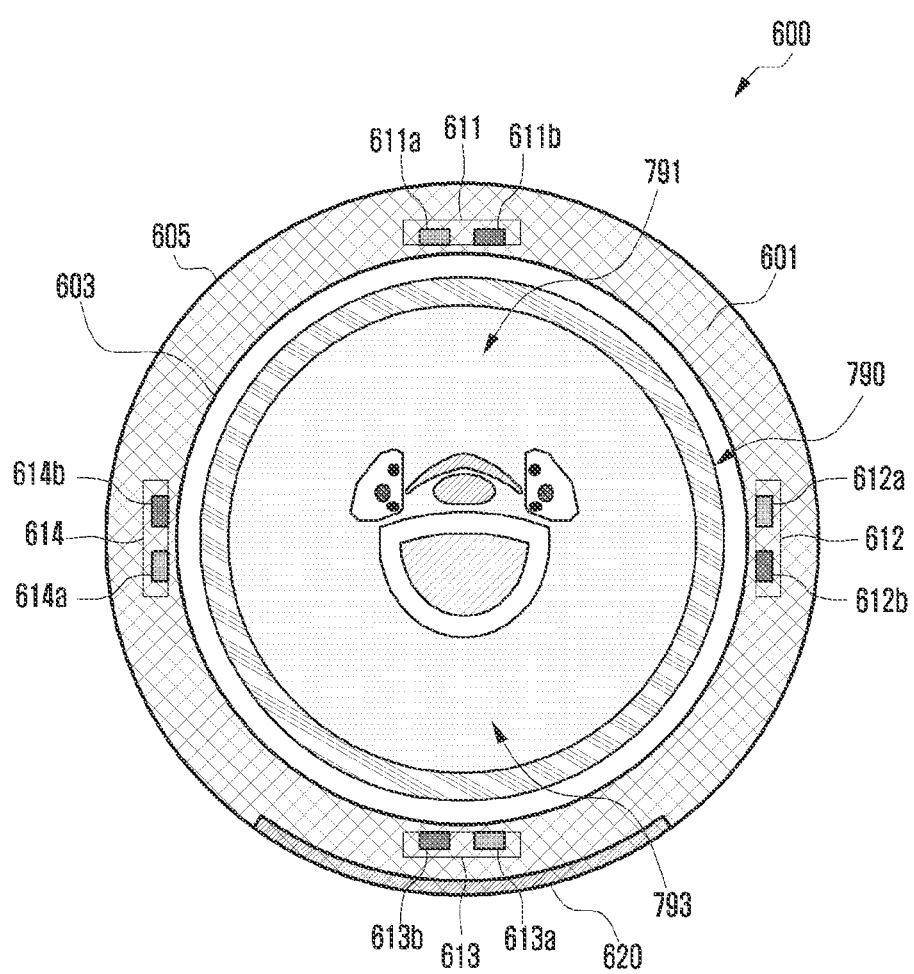
FIG. 6 is a diagram illustrating a state in which an electronic device having multiple optical sensors is worn, according to an embodiment.

FIG. 6 is a diagram illustrating a state in which an electronic device including multiple optical sensors is worn, according to an embodiment.

The structure and operation of an electronic device 600 illustrated in FIG. 6 is similar or identical to the structure of the electronic device 200 illustrated in FIGS. 2A and 2B and the operation of the electronic device 400 or 500 illustrated in FIG. 4 or 5, and a description of technical features described above are omitted below. For example, the electronic device 600 in FIG. 6 will be described with, for example, four optical sensors among multiple optical sensors as in the electronic device 500 of FIG. 5 for convenience of description.

A first surface 603 of a housing 601 of the electronic device 600 may be brought into contact with a part (e.g., a finger) of a user's body when the electronic device 600 is worn by the user, and a second surface 605 may be visually viewable from the outside. A first optical sensor 611, a second optical sensor 612, a third optical sensor 613, and a fourth optical sensor 614 of the electronic device 600 respectively include a first light emitter 611a, a second light emitter 612a, a third light emitter 613a, and a fourth light emitter 614a, each of which emits light in a designated intensity and/or a designated wavelength band. For example, each of the first light emitter 611a, the second light emitter 612a, the third light emitter 613a, and the fourth light emitter 614a may include multiple light-emitting elements (e.g., LEDs) that can output blue light having a wavelength of about 400 nm to about 550 nm, green light having a wavelength of about 450 nm to about 650 nm, red light having a wavelength of about 550 nm to about 700 nm, and/or infra-red (IR) light having a wavelength of about 880 nm to about 940 nm, respectively.

The first optical sensor 611, the second optical sensor 612, the third optical sensor 613, and the fourth optical sensor 614 of the electronic device 600 respectively include at least one first light receiver 611b, at least one second light receiver 612b, at least one third light receiver 613b, and at least one fourth light receiver 614b. For example, the at least one first light receiver 611b, the at least one second light receiver 612b, the at least one third light receiver 613b, and the at least one fourth light receiver 614b may output light signals corresponding to the amount of light which is emitted by at least one of the first light emitter 611a, the second light emitter 612a, the third light emitter 613a, and the fourth light emitter 614a, is reflected by a part of the user's body, and is received. For example, each of the first light receiver 611b, the second light receiver 612b, the third light receiver 613b, and the fourth light receiver 614b may include at least one light-receiving element (e.g., a PD, an APD, a phototransistor, or an image sensor).

The first optical sensor 611, the second optical sensor 612, the third optical sensor 613, and the fourth optical sensor 614 of the electronic device 600 are disposed on the first surface 603 of the housing 601 along the inner circumference at a designated interval.

The electronic device 600 includes a display 620 that is mounted on the second surface 605 of the housing 601 and is viewed from the outside when the user wears the electronic device 600. For example, the electronic device 600 may display various application screens, such as, for example, time information, a message notification, and a call through the display 620. In another example, the electronic device 600 may provide, through the display 620, various types of visual information related to biometric information acquired by the processor 430 or 530 of FIG. 4 or 5. For example, the display 620 may display various types of visual information generated based on biometric information or a necessary visual notification related to biometric information acquisition.

When the electronic device 600 is worn, each of the first optical sensor 611, the second optical sensor 612, the third optical sensor 613, and the fourth optical sensor 614 may be brought into contact with a part (e.g., a finger) of the user's body at a designated position or in a designated direction along the circumference of the user's finger.

For example, in the case of the ring-type wearable electronic device 600, the electronic device 600 may often rotate without being fixed to the finger of the user while being worn. The position or direction in which each optical sensor of the electronic device 600 is brought into contact with the finger may be changed over time.

FIG. 6 illustrates an example in which, while the electronic device 600 is worn on an object 790 (e.g., the user's finger) to be measured, the first optical sensor 611 among the multiple optical sensors along the circumference of the finger is positioned in the palmar-side direction 791, the second optical sensor 612 is positioned at about 90 degrees in the clockwise direction from the first optical sensor 611, the third optical sensor 613 is positioned in the dorsal-side direction 793, and the fourth optical sensor 614 is positioned at about 270 degrees in the clockwise direction from the first optical sensor 611.

A processor may separately operate each of the first optical sensor 611, the second optical sensor 612, the third optical sensor 613, and the fourth optical sensor 614. For example, the processor 430 or 530 may drive and control at least one among the first light emitter 611a, the second light emitter 612a, the third light emitter 613a, and the fourth light emitter 614a of the first optical sensor 611, the second optical sensor 612, the third optical sensor 613, and the fourth optical sensor 614, to output light. The processor 430 or 530 may receive a light signal from at least one among the first light receiver 611b, the second light receiver 612b, the third light receiver 613b, and the fourth light receiver 614b of the first optical sensor 611, the second optical sensor 612, the third optical sensor 613, and the fourth optical sensor 614.

The processor 430 or 530 may separately operate each of the first optical sensor 611, the second optical sensor 612, the third optical sensor 613, and the fourth optical sensor 614 at a different timing to receive a light signal.

The processor 430 or 530 may sequentially operate the first optical sensor 611, the second optical sensor 612, the third optical sensor 613, and the fourth optical sensor 614, to receive light signals. For example, the processor 430 or 530 may drive the first light emitter 611a to receive a light signal through the first light receiver 611b, may subsequently operate the second light emitter 612a to receive a light signal through the second light receiver 612b, may subsequently operate the third light emitter 613a to receive a light signal through the third light receiver 613b, and may subsequently operate the fourth light emitter 614a to receive a light signal through the fourth light receiver 614b. The processor 430 or 530 may sequentially drive the first light emitter 611a, the second light emitter 612a, the third light emitter 613a, and the fourth light emitter 614a at a designated interval (e.g., an interval of 0.025 see) to receive light signals through the respective light receivers.

An electronic device is provided that includes a housing, a motion sensor, and optical sensors disposed on one surface of the housing so as to be brought into contact with an object to be measured when the electronic device is worn. Each of the optical sensors comprises a respective light emitter and a respective light receiver. The electronic device also includes a sensor controller configured to control the optical sensors, and a processor operatively connected to the motion sensor and the sensor controller. The processor is configured to separately drive the optical sensors through the sensor controller to determine a respective signal characteristic of each of the optical sensors, and determine a current state of the object to be measured, based on at least one signal received through the motion sensor or the optical sensors.

The processor is also configured to drive a light emitter of at least one of the optical sensors through the sensor controller, based on the respective signal characteristics of the optical sensors according to the current state of the object to be measured, and select and receive, based on the respective signal characteristics of the optical sensors, a light signal sensed through a light receiver of at least one of the optical sensors.

The housing may include a ring type housing, and the optical sensors may be disposed at a designated interval on the inner surface of the housing.

The processor may be configured to separately receive light signals, reflected from light output by driving, through the sensor controller, respective light emitters included in at least two of the optical sensors, and sensed by the light receivers of the at least two optical sensors. When intensities of at least two of the separately received light signals are larger than a designated value, the processor may be configured to drive the optical sensors to determine the respective signal characteristic of each of the optical sensors.

The processor may be configured to receive light signals, reflected from light output by driving, through the sensor controller, light emitters included in the optical sensors at different timings and sensed by the light receivers of the optical sensors. The processor may be further configured to determine, based on the light signals, the respective signal characteristics of the optical sensors.

The processor may be further configured to analyze characteristics of the light signals to determine an optical sensor having an optimal signal characteristic from among the optical sensors.

The processor may be further configured to drive, based on the current state, a light emitter of the optical sensor having the optimal signal characteristic to emit light.

The processor may be further configured to select and receive, based on the current state, a light signal sensed through a light receiver of the optical sensor having the optimal signal characteristic, through the sensor controller.

The processor may be further configured to select and receive, based on the current state, a light signal sensed through a light receiver of an optical sensor positioned, in the housing, opposite to the optical sensor having the optimal signal characteristic, through the sensor controller.

The processor may be further configured to cause, through the sensor controller, the light emitters included in the optical sensors to emit, based on the current state, light at an identical timing. The processor may be further configured to select and receive light signals sensed by the light receivers included in the optical sensors.

The processor may be further configured to determine, based on the at least one signal received through the motion sensor or the multiple optical sensors, that the current state of the object is at least one among a normal state, a sleep state, an exercise state, and an event occurrence state.

The processor may be further configured to adjust, based on the current state, at least one of an intensity and a wavelength of at least one light emitter included in the optical sensors so as to emit light.

The processor may be further configured to, when the current state is determined to be the exercise state, separately receive light signals, which are reflected from light output by driving, through the sensor controller, the light emitters included in the optical sensors at different timings and, which are sensed by light receivers of the optical sensors.

The processor may be further configured to separately drive the optical sensors through the sensor controller for each designated period to determine the respective signal characteristic of each of the optical sensors. The processor may be further configured to determine the current state of the object, based on the at least one signal received through the motion sensor or the optical sensors.

The processor may be further configured to, when a designated event occurs according to the determination of the current state of the object, control, based on the type of the designated event, driving of the light emitter of at least one of the optical sensors through the sensor controller to emit light, and select and receive a light signal sensed through the light receiver of the at least one of the optical sensors.

Figure 7:
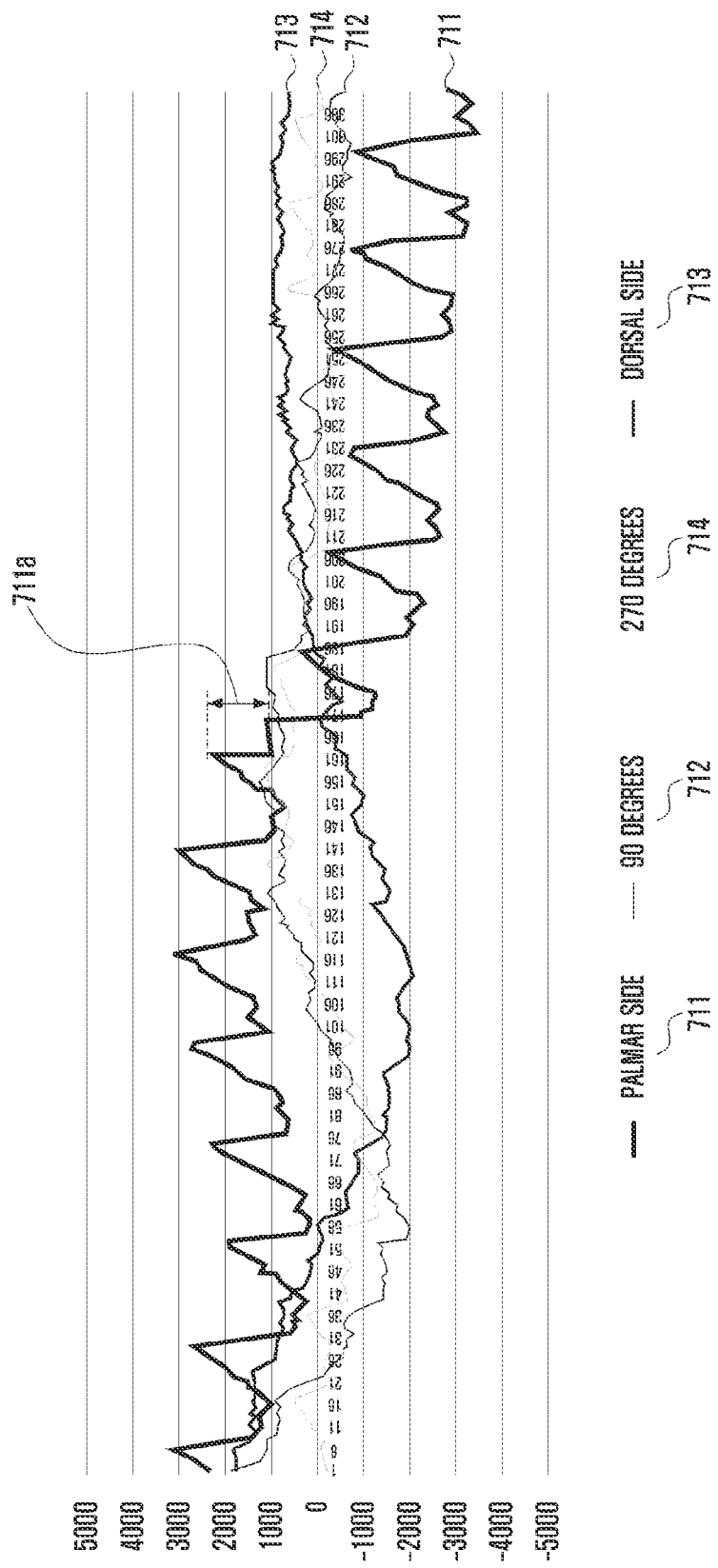
FIG. 7 is a diagram illustrating signal characteristics of multiple optical sensors of an electronic device, according to an embodiment.

FIG. 7 is a diagram illustrating signal characteristics of multiple optical sensors of an electronic device, according to an embodiment. In FIG. 7, the horizontal axis indicates the number of samples. Samples may be acquired in units of about 5 ms, and 200 samples may imply one second. In FIG. 7, the vertical axis indicates a magnitude value of a light signal.

Referring to FIG. 7, a first signal 711 indicates a light signal that has been received through the first light receiver 611b of the first optical sensor 611 positioned in the palmar-side direction by driving the first light emitter 611a of the first optical sensor 611 positioned in the palmar-side direction. A third signal 713 indicates a light signal that has been received through the third light receiver 613b of the third optical sensor 613 positioned in the dorsal-side direction by driving the third light emitter 613a of the third optical sensor 613 positioned in the dorsal-side direction. A second signal 712 indicates a light signal that has been received through the second light receiver 612b of the second optical sensor 612 by driving the second light emitter 612a of the second optical sensor 612. A fourth signal 714 indicates a light signal that has been received through the fourth light receiver 614b of the fourth optical sensor 614 by driving the fourth light emitter 614a of the fourth optical sensor 614.

A processor may analyze and compare signal characteristics of the first signal 711, the second signal 712, the third signal 713, and the fourth signal 714, which are light signals sensed through the first optical sensor 611, the second optical sensor 612, the third optical sensor 613, and the fourth optical sensor 614, respectively. The processor may determine a signal, which is the most suitable for biometric information acquisition, based on the result of comparison between the signal characteristics. For example, the signal characteristics may include the magnitude of noise (e.g., a signal-to-noise ratio (SNR) or an AC component (e.g., a peak-to-peak value).

Referring to FIG. 7 again, for example, it can be found that an AC component 711a (e.g., a peak-to-peak value) of the first signal 711, which is a light signal sensed by the first optical sensor 611 positioned in the palmar-side direction, has a largest value when compared with other signals (e.g., the second signal 712, the third signal 713, and the fourth signal 714).

The processor 430 or 530 may determine, based on the signal characteristics of light signals sensed by the first optical sensor 611, the second optical sensor 612, the third optical sensor 613, and the fourth optical sensor 614, an optical sensor that is to be used as a main sensor among the first optical sensor 611, the second optical sensor 612, the third optical sensor 613, and the fourth optical sensor 614 in order to sense a bio-signal. For example, the processor may determine that the AC component of the first signal 711, which is a light signal sensed by the first optical sensor 611, has the largest value when compared with AC components of other signals (e.g., the second signal 712, the third signal 713, and the fourth signal 714), and may determine, based on the signal characteristics, that the first optical sensor 611 is a main sensor to be used to sense a bio-signal.

When time passes, the positions of contact of multiple optical sensors with a part (e.g., a finger) of a user's body may vary depending on the motion of the electronic device, and thus, for example, the processor may drive each of the first optical sensor 611, the second optical sensor 612, the third optical sensor 613, and the fourth optical sensor 614 at a different timing at a designated time interval (e.g., every 10 minutes) or at the time of occurrence of a biometric information measurement event to determine, as described above, a signal characteristic of a light signal sensed by each optical sensor, and may determine, based thereon, a sensor to be used as a main sensor.

Figure 8:
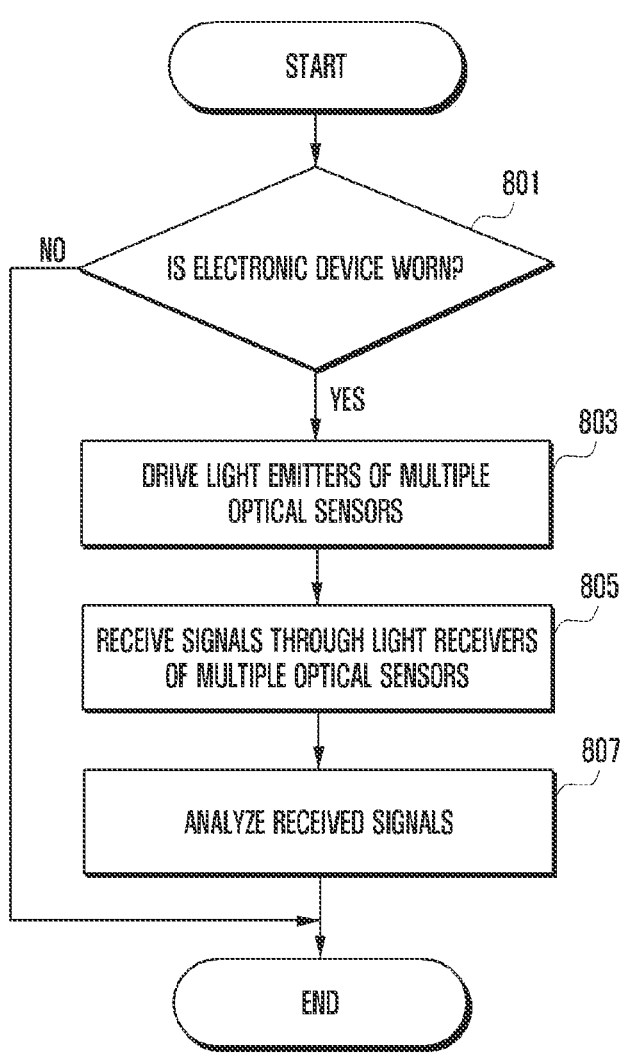
FIG. 8 is a flowchart illustrating a method for determining signal characteristics of multiple optical sensors of an electronic device, according to an embodiment.

FIG. 8 is a flowchart illustrating a method for determining signal characteristics of multiple optical sensors of an electronic device, according to an embodiment.

Operations of an electronic device including multiple optical sensors, illustrated in FIG. 8, may be performed by a processor, and, hereinafter, will be described with main reference to the structure of the electronic device 600 in FIG. 6. A description of technical features that are described in detail above, are omitted below.

At 801, the processor determines whether the electronic device is worn on a user's body.

For example, the processor may control multiple optical sensors to be separately driven. When at least two, or most, of the magnitudes of respectively received light signals have a value greater than a designated value, the processor may determine that the electronic device is in a worn state. Optical sensors that are driven in order to determine whether the electronic device is in a worn state may be all of the multiple optical sensors, or may be limited to at least two optical sensors that are designated based on each direction (e.g., four optical sensors at a 90-degree interval, or three optical sensors at a 120-degree interval) among the multiple optical sensors.

For example, the processor may control, through a sensor controller, the first optical sensor 611, the second optical sensor 612, the third optical sensor 613, and the fourth optical sensor 614 of FIG. 6 to respectively drive the first light emitter 611a, the second light emitter 612a, the third light emitter 613a, and the fourth light emitter 614a of FIG. 6, so as to emit light (e.g., IR light) having a designated intensity and/or wavelength. The processor may determine that the electronic device is in the worn state, when the magnitude of a IR light signal received through each of the first light receiver 611b, the second light receiver 612b, the third light receiver 613b, and the fourth light receiver 614b is greater than or equal to a designated value.

At 803, the processor drives the multiple optical sensors at different timings in order to determine a signal characteristic of each of the multiple optical sensors. For example, with respect to FIG. 6, the processor may sequentially drive the first light emitter 611a, the second light emitter 612a, the third light emitter 613a, and the fourth light emitter 614a of the first optical sensor 611, the second optical sensor 612, the third optical sensor 613, and the fourth optical sensor 614.

When the multiple optical sensors are sequentially driven in at 803, the processor receives, at 805, light signals sequentially sensed by the multiple optical sensors. For example, the processor may receive light signals sequentially sensed through the first light receiver 611b, the second light receiver 612b, the third light receiver 613b, and the fourth light receiver 614b of FIG. 6, respectively, when light emitted by sequentially driving the first light emitter 611a, the second light emitter 612a, the third light emitter 613a, and the fourth light emitter 614a is reflected by a part of the user's body.

At 807, the processor analyzes a signal characteristic of each of the sensed light signals. For example, the processor may analyze an AC component of each of the light signals sensed through the first light receiver 611b, the second light receiver 612b, the third light receiver 613b, and the fourth light receiver 614b of FIG. 6 to determine signal characteristics of the first optical sensor 611, the second optical sensor 612, the third optical sensor 613, and the fourth optical sensor 614.

Figure 9:
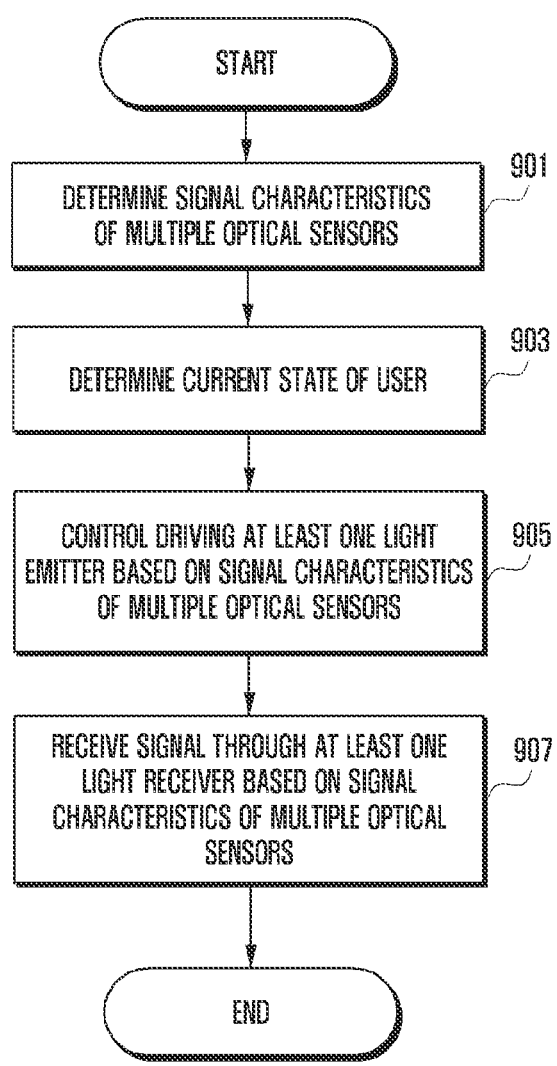
FIG. 9 is a flowchart illustrating a method for controlling multiple optical sensors of an electronic device based on signal characteristics of the multiple optical sensors, according to an embodiment.

FIG. 9 is a flowchart illustrating a method for controlling multiple optical sensors of an electronic device based on signal characteristics of the multiple optical sensors, according to an embodiment.

Operations of an electronic device including multiple optical sensors according to various embodiments, illustrated in FIG. 9, may be performed by a processor, and, hereinafter, will be described with main reference to the structure of the electronic device 600 of FIG. 6. A description of technical features described in detail above are omitted below.

At 901, the processor determines signal characteristics of multiple optical sensors. For example, the processor may analyze signal characteristics of the first optical sensor 611, the second optical sensor 612, the third optical sensor 613, and the fourth optical sensor 614 of FIG. 6, according to operations 801 to 807 of FIG. 8, and may determine, based on the analysis result, an optical sensor (e.g., the first optical sensor 611) to be used as a main sensor.

At 903, the processor determines the current state (e.g., a normal state, a sleep state, an exercise state, or a designated event occurrence state) of a user wearing the electronic device.

For example, the processor may determine, based on a sensing signal of a motion sensor, the current state (e.g., a normal state, a sleep state, an exercise state, or a designated event state) of a user wearing the electronic device. For example, the processor may determine the current state of the user to be an exercise state when it is determined, based on the sensing signal of the motion sensor, that the motion of the electronic device has a value greater than or equal to a designated first threshold value, may determine the current state of the user to be a sleep state when it is determined that the motion of the electronic device has a value less than or equal to a designated second threshold value, and may determine the current state of the user to be a normal state in the other cases. To this end, the processor may determine sensing signals of the motion sensor periodically (e.g., every 10 minutes).

For example, the processor may acquire biometric information (e.g., heart rate information) from a light signal received through at least one of the multiple optical sensors, and may determine, based thereon, the current state (e.g., a normal state, a sleep state, an exercise state, or a designated event state) of the user. To this end, the processor may periodically drive at least one optical sensor (e.g., the optical sensor determined as a main sensor) among the multiple optical sensors to receive a light signal, and may determine the current state of the user.

For example, the processor may also determine the current state (e.g., a normal state, a sleep state, an exercise state, or a designated event state) of the user wearing the electronic device, based on a sensing signal of a motion sensor and biometric information (e.g., heart rate information) acquired from a light signal received through at least one of the multiple optical sensors.

At 905, in order to acquire biometric information according to the determined current state of the user, the processor may control driving of a light emitter of at least one optical sensor selected from among the multiple optical sensors, based on the signal characteristics of the multiple optical sensors.

At 907, in order to acquire biometric information according to the determined current state of the user, the processor may receive a light signal sensed by a light receiver of at least one optical sensor selected from among the multiple optical sensors, based on the signal characteristics of the multiple optical sensors. The processor may be configured to acquire a bio-signal, based thereon. The at least one light receiver, which receives a light signal, is controlled to be identical to a light receiver of an optical sensor, which includes the at least one selected light emitter driven at 905 (e.g., the first light receiver 611*b* receives a light signal from light emitted by the first light emitter 611*a*), but may be controlled to be different from the optical sensor (e.g., the third light receiver 613*b* receives a light signal from light emitted by the first light emitter 611*a*), and the number thereof may be different (e.g., each light receiver simultaneously receives light signals from light emitted by multiple light emitters 611*a*, 612*a*, 613*a*, and 614*a*).

Figure 10A:
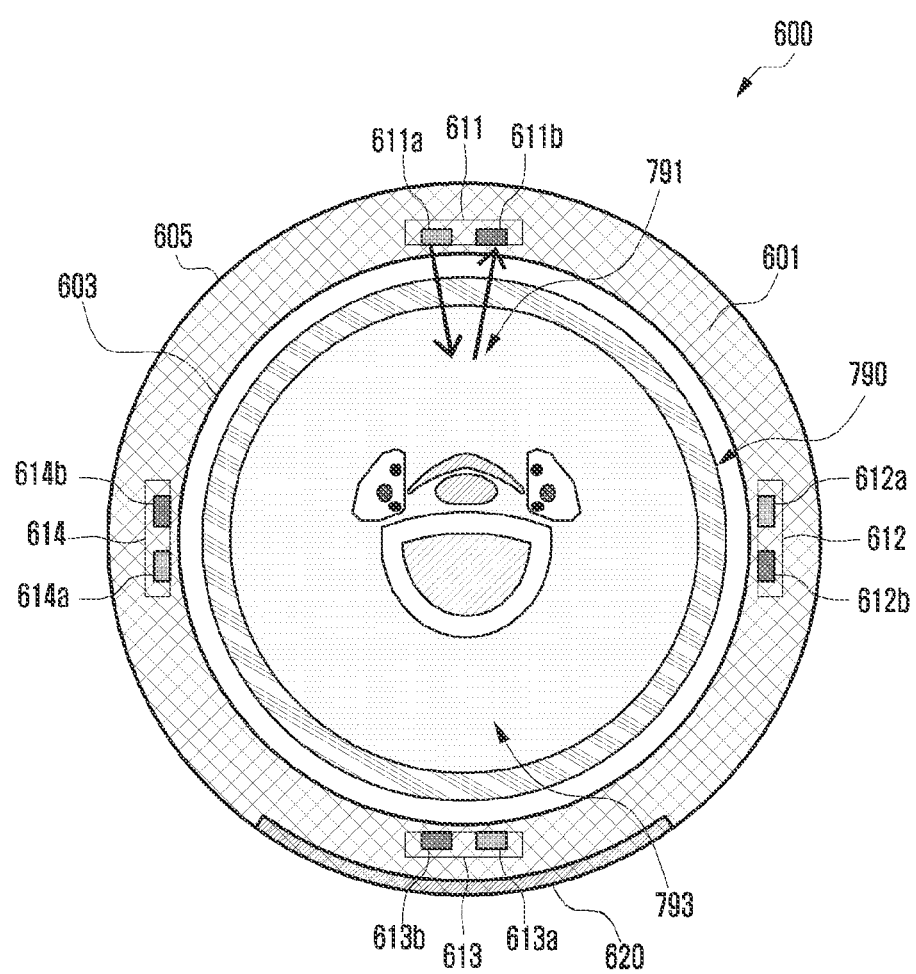
FIGS. 10A, 10B, and 10C are diagrams illustrating operations for controlling multiple optical sensors based on signal characteristics of the multiple optical sensors, according to an embodiment.
Figure 10B:
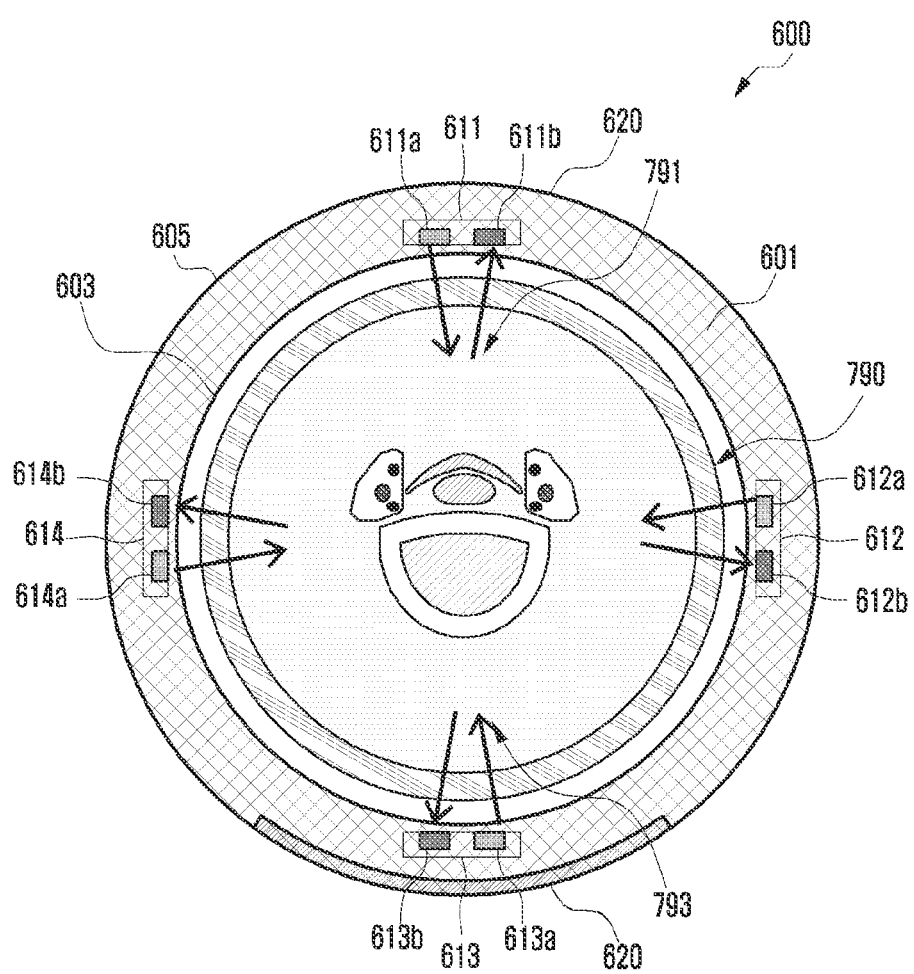
Figure 10C:
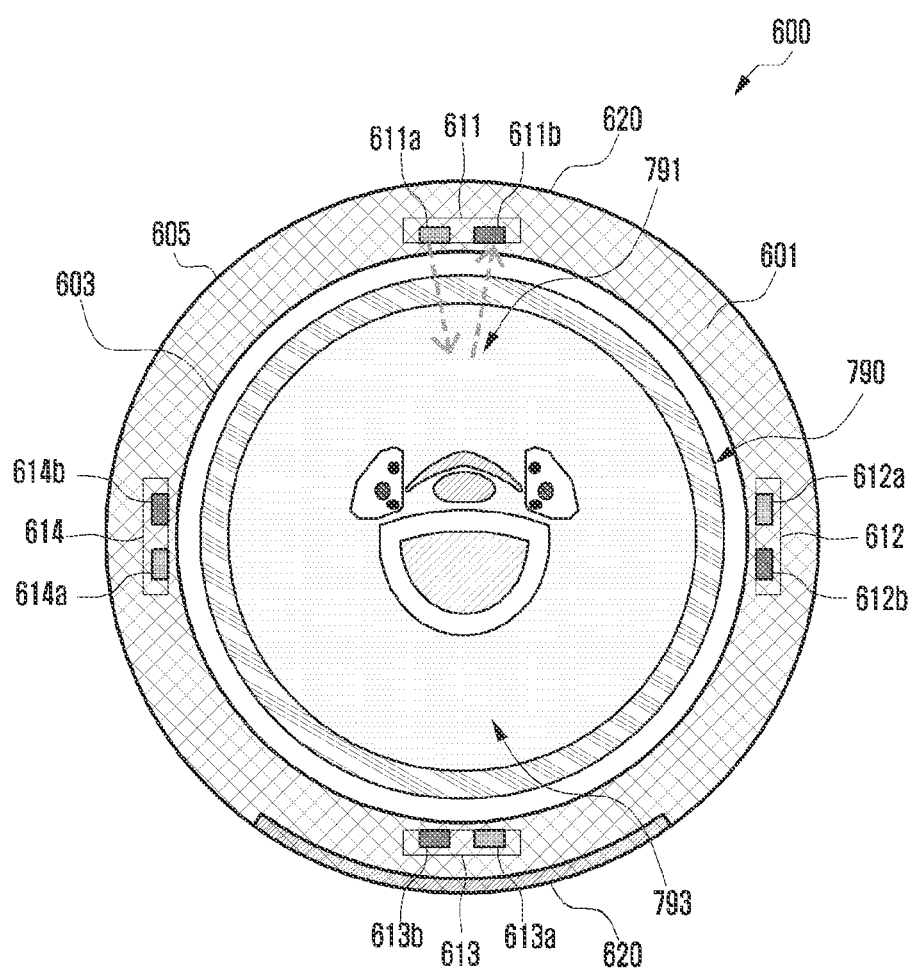

FIGS. 10A, 10B, and 10C are diagrams illustrating operations of controlling multiple optical sensors based on signal characteristics of the multiple optical sensors, according to an embodiment. In order to acquire biometric information according to the current state of a user, the processor may determine, based on signal characteristics of multiple optical sensors, the position and/or the number of light emitters of optical sensors to be driven among the multiple optical sensors. The processor may determine the driving timing, light intensity, and/or light wavelength of a light emitter to be driven.

Referring to FIG. 10A, for example, when it is determined that the current state of the user is a normal state, the processor may drive, based on the signal characteristics of the multiple optical sensors determined at 901 of FIG. 9, the first light emitter 611*a* of the first optical sensor 611 determined as a main sensor to emit light. For example, the processor may receive, through the first light receiver 611*b*, reflected light of light emitted by the first light emitter 611*a* of the first optical sensor 611.

Referring to FIG. 10B, for example, when it is determined that the current state of the user is an exercise state, the processor may drive the first light emitter 611*a*, the second light emitter 612*a*, the third light emitter 613*a*, and the fourth light emitter 614*a* of the multiple optical sensors, may receive light signals through the first light receiver 611*b*, the second light receiver 612*b*, the third light receiver 613*b*, the fourth light receiver 614*b* of the multiple optical sensors, and may acquire biometric information in consideration of all of the received light signals. For example, the first light emitter 611*a*, the second light emitter 612*a*, the third light emitter 613*a*, and the fourth light emitter 614*a* of the multiple optical sensors may be separately driven at different timings, and light signals may be separately received through the first light receiver 611*b*, the second light receiver 612*b*, the third light receiver 613*b*, and the fourth light receiver 614*b* of the multiple optical sensors. In the exercise state, the motion of the electronic device becomes more frequent, and thus, the position of contact of the multiple optical sensors with a part of the user's body may be frequently changed and signal characteristics may also be frequently changed. Therefore, it may be required to acquire as much light signal information as possible from each optical sensor. For example, the processor may control all light-emitting elements, included in each light emitter, to be driven at the time of driving of the each light emitter such that the each light emitter can emit light in as large amount as possible.

Referring to FIG. 10C, for example, when it is determined that the current state of the user is a sleep state, the processor may drive the first light emitter 611*a* of the first optical sensor 611 determined as a main sensor based on the signal characteristics of the multiple optical sensors, where a wavelength band of light to be emitted may be designated, thereby controlling the light emitter to be driven therein. For example, in order to prevent the wavelength band of light emitted in the sleep state from disturbing sleep, the processor may drive only a light-emitting element of the remaining designated wavelength band excluding a green wavelength, or may drive a red light-emitting element or an IR light-emitting element to emit only light having a red wavelength or IR wavelength.

In order to acquire biometric information, the processor may drive multiple optical sensors when a request is made or when a designated event occurs.

For example, in order to acquire biometric information at the time point of determining the current state of the user or at the time point of determining a change in the current state of the user, the processor may determine the signal characteristics of the multiple optical sensors, and may control, based on the determination, driving of a light emitter of at least one of the multiple optical sensors.

In contrast, for example, when a biometric information measurement request is made through an input module, the processor 430 or 530 may control, based on the signal characteristics of the multiple optical sensors, driving of a light emitter of at least one of the multiple optical sensors.

Furthermore, for example, the processor may periodically (e.g., every 10 minutes) measure the signal characteristics of the multiple optical sensors, and may control, based thereon, driving of a light emitter of at least one of the multiple optical sensors to acquire a bio-signal. For example, the processor may periodically determine the current state of the user. When it is determined, based on the determined current state of the user, that a designated event has occurred, the processor may control driving of a light emitter of at least one of the multiple optical sensors based on the signal characteristics of the multiple optical sensors according to the type of the designated event to emit light. The processor may select a light signal received through a light receiver of at least one of the multiple optical sensors to acquire a bio-signal. For example, the designated event may include the case in which the current state of the user of the electronic device is rapidly changed or is maintained as a designated state for a designated time or longer. A detailed description thereof is provided below with reference to FIG. 11.

Figure 11:
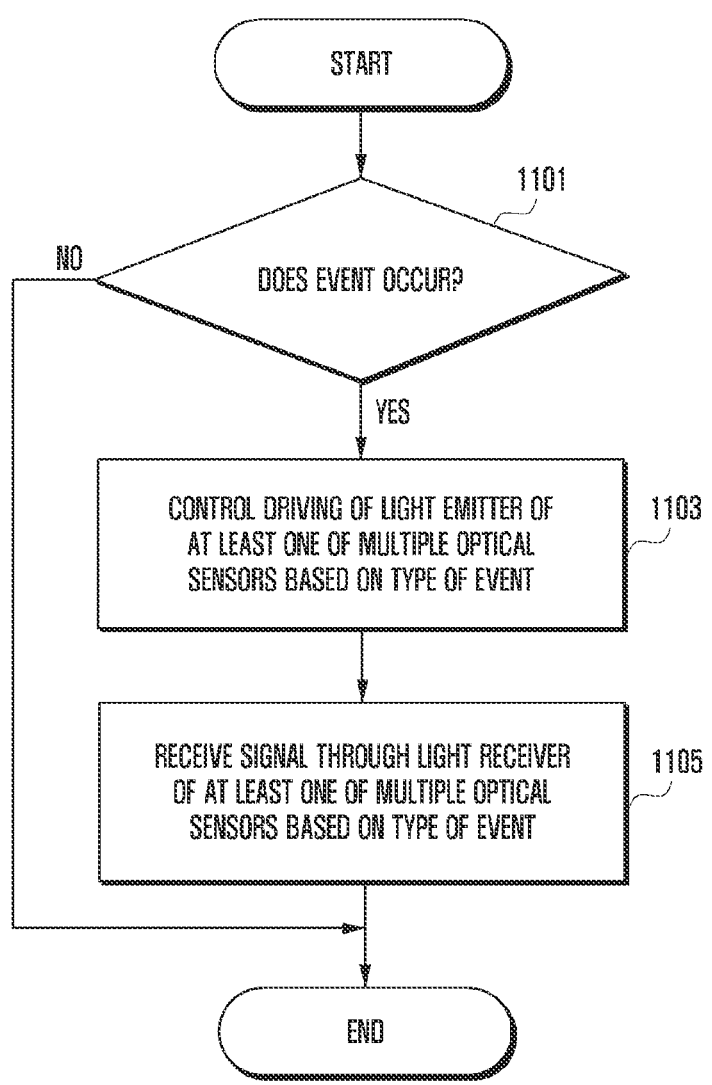
FIG. 11 is a flowchart illustrating operations for controlling multiple optical sensors of an electronic device based on designated event occurrence, according to an embodiment.

FIG. 11 is a flowchart illustrating operations of controlling multiple optical sensors of an electronic device based on designated event occurrence, according to an embodiment.

Operations of an electronic device including multiple optical sensors, illustrated in FIG. 11, may be performed by a processor, and, hereinafter, will be described with main reference to the structure of the electronic device 600 in FIG. 6. Detailed descriptions of the technical features illustrated above are omitted below.

At 1101, the processor determines whether a designated event has occurred.

For example, the processor may determine whether a designated event has occurred, based on sensor signals received through a motion sensor and/or multiple optical sensors.

For example, the occurrence of the designated event and the type of the designated event may be determined in overall consideration of change or maintenance of a sensor signal value by the motion sensor and/or the multiple optical sensors, the degree of change, time required for change, or time for which the sensor signal value remains constant. The designated event may include the case in which the motion of the electronic device rapidly increases, the case in which is a lot of the motion of the electronic device is maintained and then the motion of electronic device decreases, the case in which the motion of the electronic device, which is almost motionless, increases and then the time for which there is no motion is maintained, the case in which the time for which the motion of the electronic device is scarcely made is maintained, the case in which a heart rate is maintained in a designated interval, the case in which a heart rate is rapidly increased, or the case in which a heart rate is high but gradually decreases.

For example, considering a situation in which the user has a cough, the motion of the electronic device or the heart rate may rapidly increase. When it is determined that this type of designated event has occurred, the processor may control driving of the multiple optical sensors in order to measure, for example, $SpO_2$.

For example, considering a situation in which the user intensely exercises and then enters a recovery time, a state in which there is a lot of motion is maintained or the heart rate is maintained at a predetermined level or higher, and then the motion rapidly decreases or the heart rate gradually decreases. When it is determined that this type of designated event has occurred, the processor may control driving of the multiple optical sensors in order to measure, for example, $SpO_2$.

For example, considering a situation in which the user maintains the same posture without any motion, a state in which there is no motion of the electronic device may be maintained according to a sensor signal of the motion sensor. When it is determined that this type of designated event has occurred, the processor may control driving of the multiple optical sensors in order to measure, for example, blood pressure.

For example, considering a situation in which the user switches from a wakened state to a sleep state or from a sleep state to a wakened state, the processor may determine this event type, based on a sensor signals of the motion sensor and/or the optical sensor, and may change and control a method for driving the multiple optical sensors.

For example, considering a situation in which the user switches from a normal state to an exercise state or from an exercise state to a normal state, the processor may determine this event type, based on a sensor signal of the motion sensor and/or the optical sensor, and may change and control a method for driving the multiple optical sensors.

Referring back to FIG. 11, when it is determined that the event occurs at 1101, the processor controls driving of a light emitter of at least one of multiple optical sensors, based on the signal characteristics of the multiple optical sensors according to an event type, in order to emit light, at 1103.

At 1105, the processor acquires a bio-signal based on a signal that is received by a light receiver of at least one of the multiple optical sensors, based on the signal characteristics of the multiple optical sensors according to the event type.

Figure 12A:
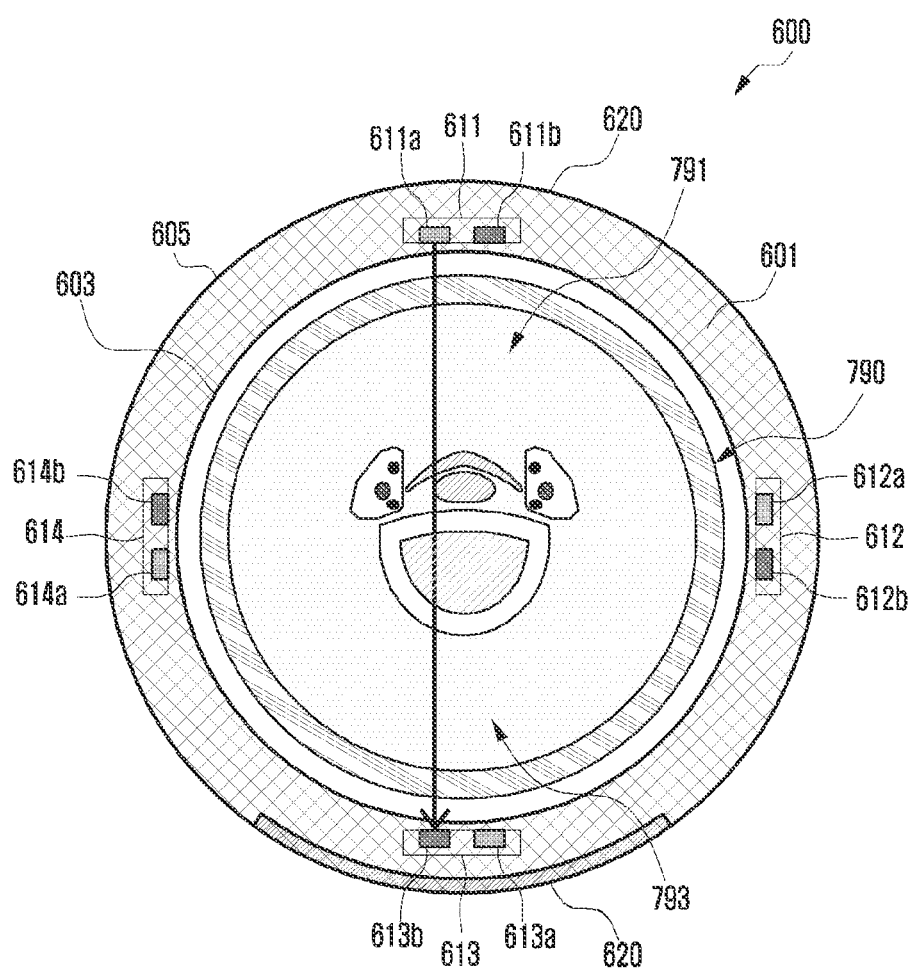
FIGS. 12A and 12B are diagrams illustrating operations for controlling multiple optical sensors based on a designated event occurrence, according to an embodiment.
Figure 12B:
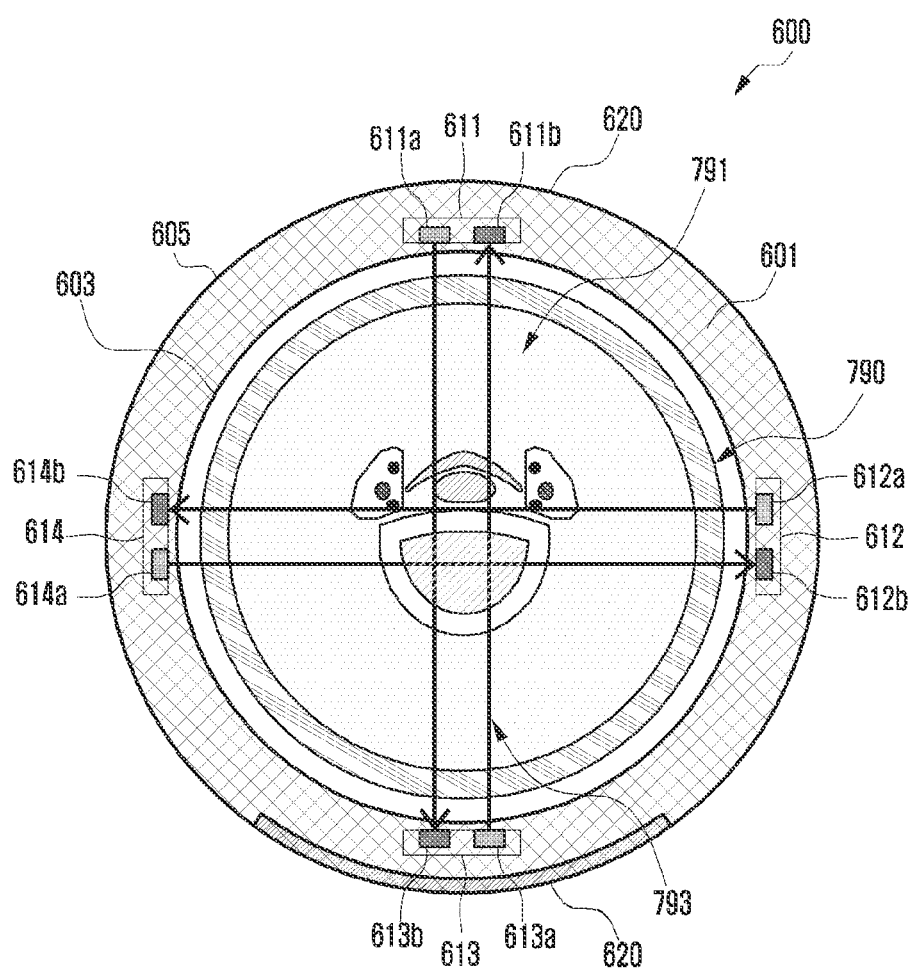

FIGS. 12A and 12B are diagrams illustrating operations of controlling multiple optical sensors based on a designated event occurrence, according to an embodiment.

Referring to FIG. 12A, in order to measure $SpO_2$ according to the event type, the processor may drive the first light emitter 611a of the first optical sensor 611 (determined as a main sensor according to the signal characteristics) to emit light, may selectively receive a light signal received by the third light receiver 613b of the third optical sensor 613 positioned in the opposite direction among the multiple optical sensors and measure $SpO_2$, based on the light signal. For example, in order to measure $SpO_2$, the processor may drive the first light emitter 611a) of the first optical sensor 611 (determined as a main sensor according to the signal characteristics) of the multiple optical sensors to sequentially emit light of a red wavelength band and light of a IR wavelength band, and may substantially simultaneously receive a light signal by the third light receiver 613b of the third optical sensor 613 positioned in the opposite direction among the multiple optical sensors and measure $SpO_2$, based on the light signal.

The received light signal may be considered emitted light that has passed through the user's body (e.g., a finger) and then received.

For example, in order to measure $SpO_2$ according to the event type, in the case of an event type in which measurement is made in an exercise state, the processor may drive, at different timings, the second light emitter 612a, the third light emitter 613a, and the fourth light emitter 614a of the second optical sensor 612, the third optical sensor 613, and the fourth optical sensor 614, in addition to the first optical sensor 611 determined as a main sensor. In response thereto, the processor may select light signals received by the fourth light receiver 614b, the first light receiver 611b, and the second light receiver 612b of the fourth optical sensor 614, the first optical sensor 611, and the second optical sensor 612, positioned in the opposite direction, and to process the selected light signals such that $SpO_2$ is obtained.

Referring to FIG. 12B, for example, in order to measure blood pressure according to an event type, the processor may substantially simultaneously drive the first light emitter 611a, the second light emitter 612a, the third light emitter 613a, and the fourth light emitter 614a of the first optical sensor 611, the second optical sensor 612, the third optical sensor 613, and the fourth optical sensor 614 to emit light in as large amount as possible, may receive all of light signals received by the first light receiver 611b, the second light receiver 612b, the third light receiver 613b, and the fourth light receiver 614b of the multiple optical sensors, respectively, and may acquire blood pressure information based on the light signals.

For example, light, which has been substantially simultaneously emitted from all light emitters (e.g., the first light emitter 611a, the second light emitter 612a, the third light emitter 613a, and the fourth light emitter 614a), and has been reflected or has passed through a part (e.g., a finger) of the user's body, may be sensed by light receivers (e.g., the third light receiver 613b, the fourth light receiver 614b, the first light receiver 611b, and the second light receiver 612b in order) disposed at opposite positions, respectively, and blood pressure may be measured in overall consideration of the sensed signal values. Therefore, the amount of light can be maximally ensured and multiple light signals can be simultaneously acquired, thereby minimizing noise and reducing time necessary for blood pressure measurement.

While the disclosure has been shown and described with reference to certain embodiments therefor, it will be understood by those skilled in the art that various changes in form and detail may be made therein without departing from the scope of the disclosure. Therefore, the scope of the disclosure should not be defined as being limited to the embodiments, but should be defined by the appended claims and equivalents thereof.

What is claimed is:

1. An electronic device comprising:
   a ring-type housing;
   at least one motion sensor;
   a plurality of light emitters and a plurality of light receivers disposed along a circumference of the ring-type housing at different directions to each other and configured to emit and receive lights through an inner surface of the ring-type housing to be in contact with a finger of a user wearing the electronic device, the plurality of light emitters including a first wavelength band light emitter, a second wavelength band light emitter, and a third wavelength band light emitter; and
   processing circuitry operatively connected to memory, the at least one motion sensor, the plurality of light emitters and the plurality of light receivers,
   wherein instructions stored in the memory, when executed by the processing circuitry, cause the electronic device to:
      determine whether a current state of the user is a sleep state or an exercise state based on signals received through the at least one motion sensor and the plurality of light receivers;
      in case that the current state of the user is the sleep state, selectively drive a first number of the plurality of light emitters to acquire biometric information; and
      in case that the current state of the user is the exercise state, selectively drive a second number of the plurality of light emitters to acquire the biometric information, wherein the first number is different from the second number.

2. The electronic device of claim 1, wherein instructions stored in the memory, when executed by the processing circuitry, cause the electronic device to, when the current state of the user is determined as the exercise state:
   drive at least two of the plurality of light emitters to output light, and
   receive, via at least two of the plurality of light receivers, light emitted by the at least two of the plurality of light emitters and reflected by the finger of the user to acquire biometric information.

3. The electronic device of claim 1, wherein instructions stored in the memory, when executed by the processing circuitry, cause the electronic device to, when the current state of the user is determined as the sleep state:
   drive at least one of the plurality of light emitters to output light, wherein the at least one of the plurality of light emitters comprises the first wavelength band light emitter or the second wavelength band light emitter and excludes the third wavelength band light emitter, and
   receive, via at least one of the plurality of light receivers, light emitted by the at least one of the plurality of light emitters and reflected by the finger of the user to acquire biometric information.

4. The electronic device of claim 3, wherein the first wavelength band light emitter includes an infra-red light emitter, the second wavelength band light emitter includes a red light emitter, and the third wavelength band light emitter includes a green light emitter.

5. The electronic device of claim 1, wherein instructions stored in the memory, when executed by the processing circuitry, cause the electronic device to selectively drive at least one of the plurality of light emitters based on the state of the user to acquire heart rate or SpO2.

6. A method of controlling an electronic device having a ring-type housing, at least one motion sensor, and a plurality of light emitters and a plurality of light receivers disposed along a circumference of the ring-type housing at different directions to each other and configured to emit and receive lights through an inner surface of the ring-type housing to be in contact with a finger of a user wearing the electronic device, the plurality of light emitters including a first wavelength band light emitter, a second wavelength band light emitter, and a third wavelength band light emitter, the method comprising:
   determining whether a current state of the user is a sleep state or an exercise state based on signals received through the at least one motion sensor and the plurality of light receivers;
   in case that the current state of the user is the sleep state, selectively driving a first number of the plurality of light emitters to acquire biometric information; and
   in case that the current state of the user is the exercise state, selectively driving a second number of the plurality of light emitters to acquire the biometric information, wherein the first number is different from the second number.

7. The method of claim 6, wherein the selectively driving comprises, when the current state of the user is determined as the exercise state:
   driving at least two of the plurality of light emitters to output light, and
   receiving, via at least two of the plurality of light receivers, light emitted by the at least two of the plurality of light emitters and reflected by the finger of the user to acquire biometric information.

8. The method of claim 6, wherein the selectively driving comprises, when the current state of the user is determined as the sleep state:
   driving at least one of the plurality of light emitters to output light, wherein the at least one of the plurality of light emitters comprises the first wavelength band light emitter or the second wavelength band light emitter and excludes the third wavelength band light emitter, and
   receiving, via at least one of the plurality of light receivers, light emitted by the at least one of the plurality of light emitters and reflected by the finger of the user to acquire biometric information.

9. The method of claim 8, wherein the first wavelength band light emitter includes an infra-red light emitter, the second wavelength band light emitter includes a red light emitter, and the third wavelength band light emitter includes a green light emitter.

10. The method of claim 6, wherein the selectively driving selectively drives at least one of the plurality of light emitters based on the state of the user to acquire heart rate or SpO2.

11. An electronic device comprising:
    a ring-type housing;
    at least one motion sensor;
    a plurality of light emitters and a plurality of light receivers disposed along a circumference of the ring-type housing at different directions to each other and configured to emit and receive lights through an inner surface of the ring-type housing to be in contact with a finger of a user wearing the electronic device, the plurality of light emitters including an infra-red light emitter, a red light emitter, and a green light emitter; and processing circuitry operatively connected to memory, the at least one motion sensor, the plurality of light emitters and the plurality of light receivers, wherein instructions stored in the memory, when executed by the processing circuitry, cause the electronic device to:

determine whether a current state of the user is a sleep state or an exercise state based on signals received through the at least one motion sensor and the plurality of light receivers;

in case that the current state of the user is determined asan the exercise state:

drive a first number of the plurality of light emitters to output light, and receive, via at least two of the plurality of light receivers, light emitted by the first number of light emitters and reflected by the finger of the user to acquire biometric information; and in case that the current state of the user is determined asa the sleep state:

drive a second number of the plurality of light emitters to output light, wherein the second number of the plurality of light emitters comprises an infra-red light emitter or a red light emitter and excludes a green light emitter, and receive, via at least one of the plurality of light receivers, light emitted by the second number of the plurality of light emitters and reflected by the finger of the user to acquire biometric information, wherein the first number is different from the second number.

* * * * *